United States Patent [19]

Tanaka et al.

[11] Patent Number: 5,013,243

[45] Date of Patent: May 7, 1991

[54] DENTURE ATTACHMENT

[75] Inventors: Yoshinobu Tanaka; Yoshiro Iwama; Yoshinobu Honkura; Kazuo Arai; Aki Watarai, all of Aichi, Japan

[73] Assignee: Aichi Steel Works, Limited, Araocho, Japan

[21] Appl. No.: 460,073

[22] PCT Filed: Jun. 1, 1989

[86] PCT No.: PCT/JP89/00548
§ 371 Date: Jan. 29, 1990
§ 102(e) Date: Jan. 29, 1990

[87] PCT Pub. No.: WO89/11835
PCT Pub. Date: Dec. 14, 1989

[30] Foreign Application Priority Data

Jun. 1, 1988 [JP] Japan ............................... 63-134737
May 10, 1989 [JP] Japan ............................... 64-116595
May 10, 1989 [JP] Japan ............................... 64-116596

[51] Int. Cl.$^5$ .............................................. A61C 13/235
[52] U.S. Cl. .................................................... 433/189
[58] Field of Search .......................................... 433/189

[56] References Cited

U.S. PATENT DOCUMENTS

| 4,431,419 | 2/1984 | Portnoy | 433/189 |
| 4,508,507 | 4/1985 | Jackson | 433/189 |
| 4,815,975 | 3/1989 | Garrel et al. | 433/189 |
| 4,824,371 | 4/1989 | Deutsch et al. | 433/189 |
| 4,911,640 | 3/1990 | Schwab | 433/189 |

FOREIGN PATENT DOCUMENTS 57-164053 10/1982 Japan.
57-170246 10/1982 Japan.
62-16759 1/1987 Japan.
62-231653 10/1987 Japan.

*Primary Examiner*—John J. Wilson
*Attorney, Agent, or Firm*—Blum Kaplan

[57] ABSTRACT

A denture attachment including a magnet body, to be embedded in a denture base, comprises a pair of soft magnetic alloy end plates, a non-magnetic alloy spacer disposed between the end plates, and a cap covering the magnet body, the end plates and the spacer except on the side of a coping. The attachment causes a magnetic attractive force of the magnet body to act on the coping of a soft magnetic alloy embedded in a pulp cavity of a tooth deprived of the crown, whereby the denture base is stabilized on gingiva. The magnet body is disposed with its N and S poles facing the end plates, respectively.

12 Claims, 10 Drawing Sheets

DENTURE ATTACHMENT

DESCRIPTION

1. Technical Field

The present invention relates to a denture attachment utilizing a magnetic attractive force. More particularly, the present invention relates to a denture attachment to be embedded in a denture base, which comprises a magnet body to produce a magnetic attractive force between the magnet body and a soft magnetic alloy coping embedded in the root of a tooth, thereby enabling stable attachment of the denture in an oral cavity.

2. Background Art

In using a denture by removing a damaged crown of a tooth, there has been used a denture such that a coping of a soft magnetic alloy formed with a flat surface along the top portion of the gingiva is fixedly embedded in a top portion of the root of the tooth left in the gingiva, whereas the magnet body is embedded in the denture base at a position corresponding to the coping, to hold the denture base stably on the gingiva by utilizing the magnetic attractive force of the magnet body.

In the case, as shown in FIG. 1, where the crown penetrating through the gingiva 91 is removed to leave the root 92 alone, a coping 93 formed of a soft magnetic alloy and provided with a flat surface at the top thereof is fixedly embedded in the pulp cavity of the root 92. On the other hand, a denture has a denture base 94 formed of a plastic or the like, with a hard denture portion 95 fixed at a position opposed to the coping 93, and a denture attachment 10 is fixedly embedded in the denture base 94 at a position opposed to the coping 93.

For attaching this type of denture utilizing the magnetic attractive force, a denture attachment as shown at numeral 8 in FIG. 2 has hitherto been proposed [Japanese Patent Application Laid-Open (KOKAI) No. 62-231653]. The denture attachment 8, as shown in FIG. 2, comprises a magnet 82 disposed in a stainless steel casing 81 having a projection 83 at an upper portion. As the magnet body 82, a rear-earth permanent magnet based on, for instance, Sm-Co (samarium-cobalt) having a strong magnetic force has been used.

All the conventional magnet bodies, however, have low magnetic attractive forces of about 200 to 300 g. These attractive forces are lower, as compared with the mechanical holding forces of at least 500 g exerted by the springs conventionally used for fastening a denture base to a tooth in an oral cavity.

Besides, the magnet body is liable to be corroded in the oral cavity; therefore, where the rare-earth permanent magnet is exposed in the oral cavity, the magnet body will rust with the result of a rapid lowering in the attractive force and generation of safety problems. Where rust prevention is attempted by covering entirely the magnet body with a casing made of a non-magnetic alloy such as stainless steel, as described in the above-mentioned patent application, the attractive force is lowered due to the presence of the casing made of the non-magnetic alloy between the magnet body and the coping.

Furthermore, there is a proposal for making the rare-earth permanent magnet as a sintered body of powder and protecting the sintered body with a foil of a non-magnetic alloy similarly to the above, but this proposal is impracticable because the foil of the non-magnetic alloy is broken due to the direct contact with the coping.

DISCLOSURE OF THE INVENTION

It is accordingly a primary object of the present invention to provide a denture attachment small in size and having a high attractive force as well as excellent corrosion resistance and wear resistance.

Namely, a denture attachment according to the present invention comprises a magnet body of a rare-earth permanent magnet disposed between a pair of end plates which are arranged perpendicularly to a coping embedded in a root portion of a tooth, a spacer of a non-magnetic alloy disposed beneath the magnet body, and a cap covering these members except the coping side of the end plates and the spacer, with the spacer and the cap being joined to the end plates.

Of each of the pair of end plates, an inner surface opposed to the magnet body is formed as a flat surface, whereas an outer surface to be covered by the cap is formed as a cylindrical or prismatic surface bulged outward. A first side surface of the spacer and a first side surface of the magnet body opposed to the end plates are each formed as a flat surface to be brought into contact with a flat inner surface of the end plate. Second side surfaces of the spacer and the magnet body, on the other hand, are each formed as a cylindrical or prismatic surface for smooth contiuity with an outer surface of the end plate. End faces on one side of the pair of end plates are located flush with an end face of the spacer. Further, end faces on the other side of the pair of end plates are located flush with an end face of the magnet body.

To attain the above-mentioned object, a rare-earth permanent magnet having a maximum energy product of at least 20 MGOe is recommendably used for the magnet body, whereas a soft magnetic alloy having a saturation magnetic flux density of at least 13000 G and a permeability of at least 3000 is recommendably used for the end plates, and non-magnetic alloy having a permeability of not more than 1.2 are recommendably used for the spacer and the casing. Furthermore, when the end plates are each formed of a soft magnetic alloy having a saturation magnetic flux density of at least 20,000 G and provided with a rustproof plating on the surface thereof for contact with the coping, a denture attachment with a further higher attractive force is obtainable.

It is another object of the present invention to provide a denture attachment of the above-mentioned type in which the joint portions of the cap and the end plates and the joint portions of the end plates and the spacer are perfectly sealed against corrosion by saliva and have further higher strength and durability.

To attain the object, according to the present invention, the jointing of the boundary surfaces of the cap, end plates and spacer on the side of the coping is made by either laser welding or electron beam welding.

In the above denture attachment, the height of the spacer is 0.05 to 1.00 mm, and the depth of weld penetration at the joint portions is at least 0.02 mm and not more than the height of the spacer. To ensure favorable formation of the joint portions, it is recommendable to use a corrosion-resistant soft magnetic alloy containing, by weight, up to 0.03% of C, 11 to 30% of Cr and up to 4% of Mo for the end plates, and to use Ti, a Ti alloy or a non-magnetic stainless steel containing up to 0.03% of C for the spacer and the cap.

It is a further object of the present invention to provide a denture attachment of the above-mentioned type which has a reduced size and a further enhanced magnetic attractive force per unit volume.

To attain the object, a denture attachment according to the present invention comprises a denture attachment main body composed of an assembly of a pair of end plates, a spacer and a magnet body but not including a cap, wherein the dimensions of the end plates, spacer and magnet body are so determined that, assuming that the height of the end plates is H (mm), the area of section perpendicular to the height direction of the end plates, of the above-mentioned peripheral surface, is S (mm$^2$), the maximum and minimum radii measured from the center of the section are a (mm) and b (mm), respectively, and the sectional area of the magnet body in the above-noted section is Sm (mm),
then the values X, Y and Z defined as X=b/a, Y=Sm/S, and Z=H/S satisfy the following inequality:

$$\frac{(X - 0.75)^2}{0.25^2} + \frac{(Y - 0.4)^2}{0.35^2} + \frac{(Z - 0.15)^2}{0.1^2} \leq 1.$$

Further, to attain the above object, it is recommendable to remove a shoulder portion of the end plate in a volume ratio of up to 25% based on the volume S·H (mm$^2$) obtained by multiplying the sectional area S by the height H of the end plate.

BEST MODE FOR CARRYING OUT THE INVENTION

Denture Attachment

Figure 3:
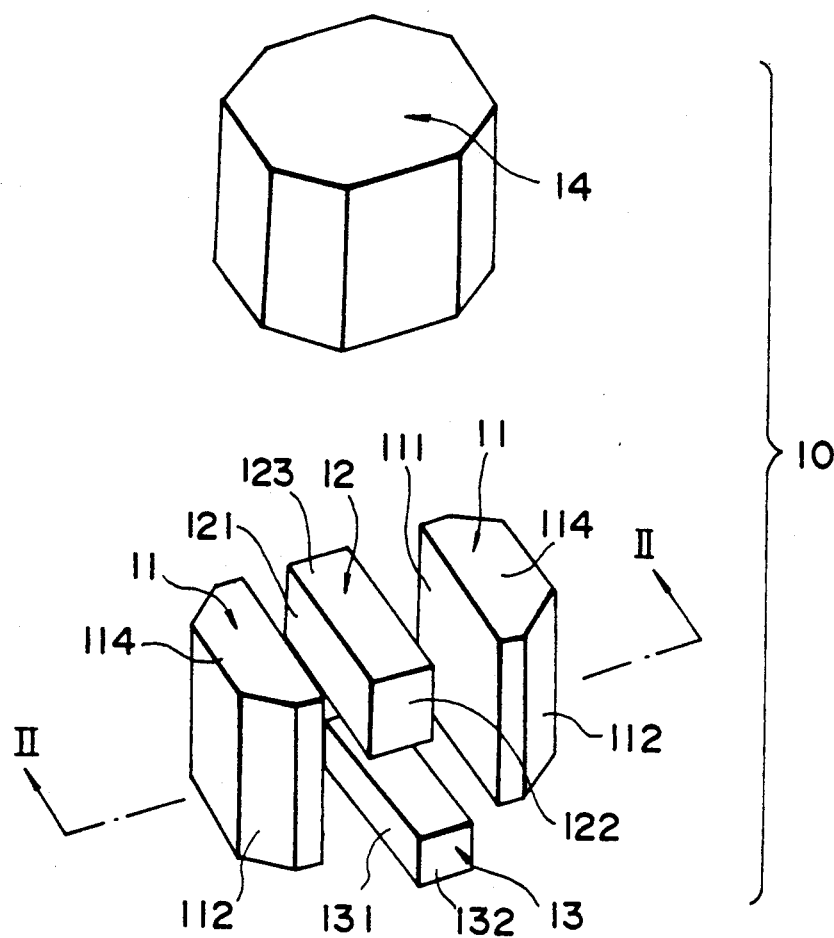
FIG. 3 is an exploded perspective view of one embodiment of a denture attachment according to the present invention.
Figure 4:
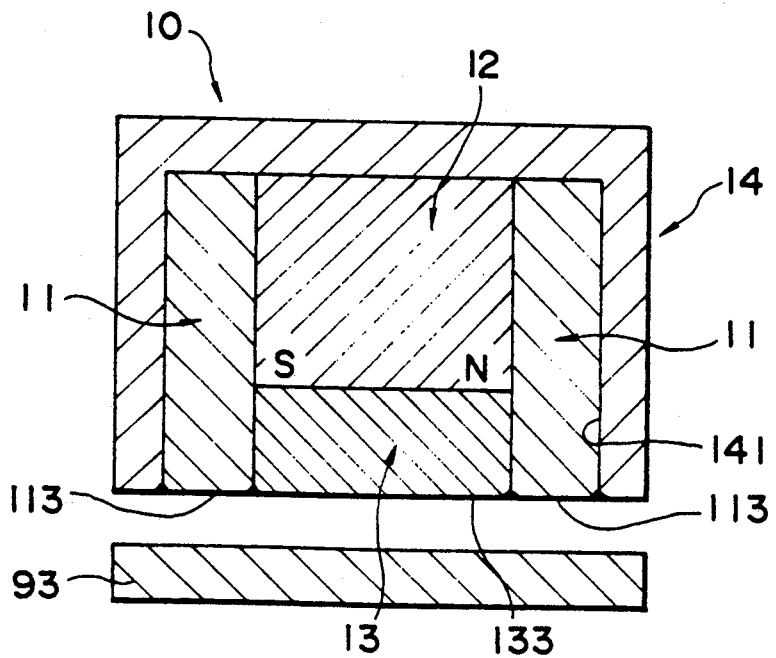
FIG. 4 is a sectional view taken along line II—II of FIG. 3.

A denture attachment according to the present invention, as shown in FIGS. 3 and 4, comprises a pair of end plates 11, 11 arranged perpendicularly to an opposed surface of a coping 93, a spacer 13 disposed between the end plates at a lower position, a magnet body 12 superposed on the spacer 13, and a cap 14 covering the periphery of these members except on the side of the coping 93. The magnet body 12 is so disposed that the direction of a straight line connecting between the S pole and the N pole is parallel to the top surface of the coping. The end plates 11 are made by use of a corrosion-resistant soft magnetic alloys, whereas the spacer 13 and the cap 14 are made by use of non-magnetic alloys.

As the magnet body, a rare-earth permanent magnet having a maximum energy product of at least 20 MGOe (mega gauss oersted) is preferably used. It is thereby possible to obtain an attachment having an attractive force of at least about 500 g. Examples of such a rare-earth permanent magnet include Sm-Co alloys, such as SmCo$_5$, Sm$_2$Co$_{17}$, etc., and Nb-Fe-B alloys.

As the soft magnetic alloy constituting the end plates, a soft magnetic alloy having a saturation magnetic flux density of at least 13,000 G and a permeability of at least 3000 is preferably used. Examples of the soft magnetic alloy having such a characteristic include pure iron, 13Cr-2Mo steels, 17Cr-2Mo steels, etc. When a soft magnetic alloy having a saturation magnetic flux density of at least 20,000G is used for the end plates, the attractive force is further increased, pure iron being an example of such a soft magnetic alloy.

As non-magnetic alloys constituting the spacer and the cap, non-magnetic alloys having a permeability of not more than 1.2 are preferably used. Examples of the non-magnetic alloy having such a characteristic include 17Cr-12Ni-2Mo steels, titanium alloys, etc.

Moreover, it is preferable to apply a corrosion-resistant rustproof plating to the lower surface of the denture attachment, namely, the surface opposed to the coping. The rustproof plating may be a chromium (Cr) plating, with a film thickness of 5 to 30 82 m, electroless plating or the like. Furthermore, to enhance the chemical durability of the attachment, the boundary surfaces of the cap and the end plates and the boundary surfaces of the end plates and the spacer, on the side of the coping, are respectively joined together by brazing or welding.

In the denture attachment according to the present invention, the magnet body of a rare-earth permanent magnet is disposed between the pair of end plates perpendicular to the coping, and the spacer of non-magnetic alloy is disposed on the lower surface (the surface facing the coping) of the magnet body. Therefore, it is possible to generate a large attractive force between the two end plates and coping. Namely because soft magnetic alloys are used for the coping and the pair of and plates, a closed magnetic circuit is formed, thereby enhancing the attractive force between the coping and the denture attachment. The greater the maximum energy product of the rare-earth permanent magnet, the greater the attractive force.

Besides the spacer and the cap are not present between the end plates and the coping, and are each formed of a non-magnetic alloy, so that they do not disturb the magnetic forces acting between the coping and the end plates. It is therefore possible to secure normal strong attractive forces. The excellent attractive force enables a smaller design, too.

In addition, the denture attachment is covered with the casing, except on the side of the coping, and the lower side of the magnet disposed between the end plates is shut off by joining the boundary surfaces of the end plates, spacer and cap. It is thus possible to obtain excellent corrosion resistance. Moreover, because the pair of end plates and the spacer make contact with the coping so that the magnet body does not make direct contact with the coping, good wear resistance is displayed.

As mentioned above, according to the present invention it is possible to obtain a small denture attachment having excellent attractive force, corrosion resistance and wear resistance.

The denture attachment according to the present invention will now be explained with main regard to structure, referring to FIGS. 3 and 4.

The attachment comprises a pair of end plates 11, 11 arranged perpendicularly to a coping 93, a spacer 13 provided at a lower position between the end plates 11, 11, and a magnet body 12 placed on the spacer 13, and the entire peripheral surface of the attachment except the lower surface opposed to the coping is covered by a boxlike cap 14. It should be noted that the magnet body 12 is disposed with the S and N poles thereof facing the end plates 11, 11, respectively.

The pair of end plates 11, 11 are formed in substantially the same shape. Of each of the end plates 11, 11, an inner surface 111 opposed to the magnet body 12 is formed as a flat surface, whereas an outer surface to be covered by the cap 14 is formed as a cylindrical or prismatic surface bulged outward. The outer surfaces 112, 112 of the end plates 11, 11 shown in FIG. 4 are each formed to constitute a part of the outer surfaces of an octagonal prism.

The spacer 13 is formed as columnar body with a rectangular cross-sectional shape, of which first surfaces 131, 131 opposed to the end plates 11, 11 are formed as flat surfaces, whereas second side surfaces 132, 132 at longitudinally end portions are formed as cylindrical or prismatic surfaces for smooth contiuity with the cylindrical or prismatic outer surfaces 112, 112 of the end plates 11, 11. Namely, when the spacer 13 is disposed sandwiched between the pair of end plates 11, 11, the first side surfaces 131, 131 of the spacer 13 make close contact with the inner surfaces 111, 111 of the end plates 11, 11, whereas the second side surfaces 132, 132 of the spacer 13 are connected smoothly to the cylindrical or prismatic outer surfaces 112, 112 of the end plates 11, 11 to form a predetermined cylindrical or prismatic surface. The second side surfaces 132, 132 shown in FIG. 4 each constitute a part of a flat surface portion of the octagonal prism.

The magnetic body 12 is formed as a columnar body with a rectangular cross-sectional shape and with substantially the same plan-view shape as the spacer 13. Of the magnet body 12, first side surfaces 121, 121 opposed to the end plates 11, 11 are formed as flat surfaces, whereas second surfaces 122, 122 at longitudinal end portions are formed as cylindrical or prismatic surfaces for smooth continuity with the cylindrical or prismatic outer surfaces 112, 112 of the end plates 11, 11. Namely, when the magnet body 12 is disposed sandwiched between the pair of end plates 11, 11, the first side surfaces, 121, 121 of the magnet body 12 make close contact with the inner surfaces 111, 111 of the end plates 11, 11, whereas the second side surfaces 122, 122 are connected smoothly to the cylindrical or prismatic outer surfaces 112, 112 of the end plates 11, 11 to form a predetermined cylindrical prismatic surface. The second side surfaces 122, 122 shown in FIG. 4 each constitute a part of a flat surface portion of one face of the octagonal prism.

The spacer 13 and the magnet body 12 are sandwiched, in a superposed state, between the pair of end plates 11, and the total height of the spacer 13 and the magnet body 12 is set to be equal to the height of the end plates 11. End faces 113, 113, at one end with respect to the height direction, of the end plates 11 facing the coping 93 are formed as flat surfaces perpendicular to the height direction, and are disposed flush with an end face 133 of the spacer 13. End faces 114, 114, at the other end with respect to the height direction, of the end plates 11 are disposed flush with an end face 123 of the magnet body 12.

The cap 14 has at least an inner peripheral surface 141 thereof formed in such a shape as to make close contact with the cylindrical or prismatic surface constituted of the outer surfaces 112, 112 of the end plates 11, the second side surfaces 132 of the spacer 13 and the second side surfaces 122 of the magnet body 12.

A soft magnetic alloy is used for the coping 93, a corrosion-resistant soft magnetic alloy for the end plates 11, 11, corrosion-resistant non-magnetic alloys for the spacer 13 and the cap 14, and a rare-earth permanent magnet for the magnet body 12. At the bottom surface of the denture attachment, the boundary surfaces of the cap, spacer and end plates are brazed to each other.

Figure 1:
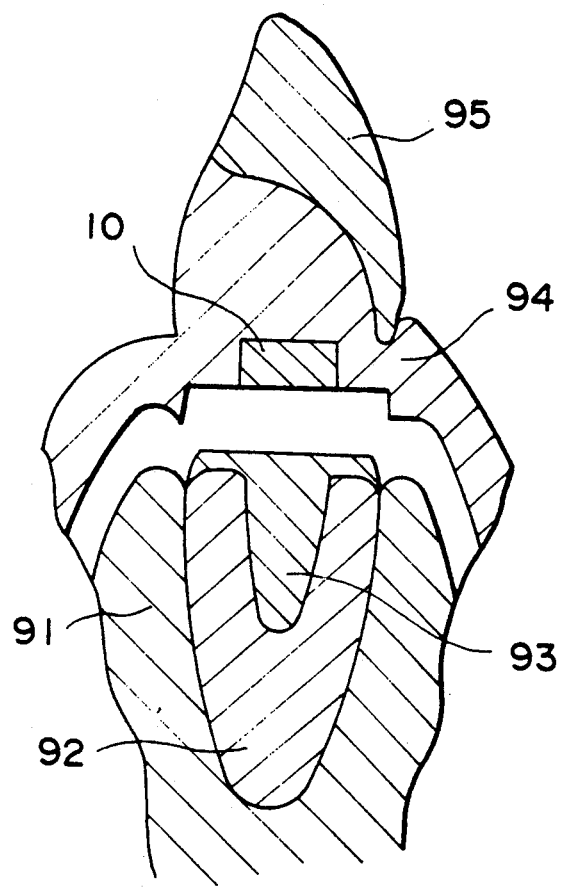
FIG. 1 is a sectional illustration of a denture attachment in the state of being embedded in a denture base oppositely to a coping attached to a root portion of a tooth.
Figure 2:
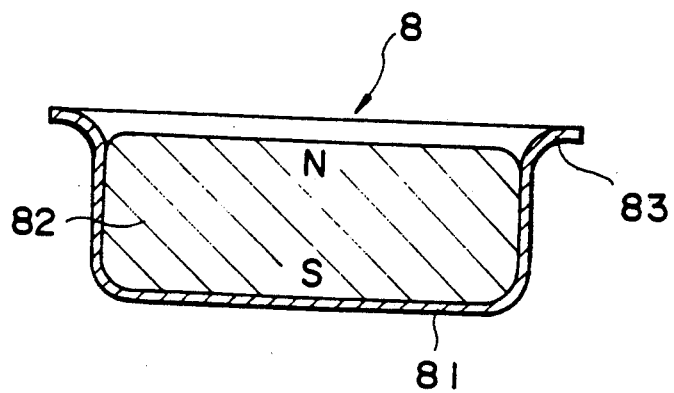
FIG. 2 is a sectional view of a denture attachment according to the prior art.

The denture attachment is about 5 mm in height and in length, and is about 4 mm in width. The dimensions are determined appropriately according to the dimensions of the denture base 94 (FIG. 1) in which the attachment is embedded. Though the substantially prismatic attachment has been illustrated in this embodiment, the shape of the attachment may be arbitrarily selected, for instance, a circular cylinder, an elliptic cylinder or a deformed column. The denture attachment according to the present invention is embedded in the denture base 94, with the end faces 113 of the end plates 11 and the end face 133 of the spacer 13 exposed to the surface of the denture base 94.

Figure 5:
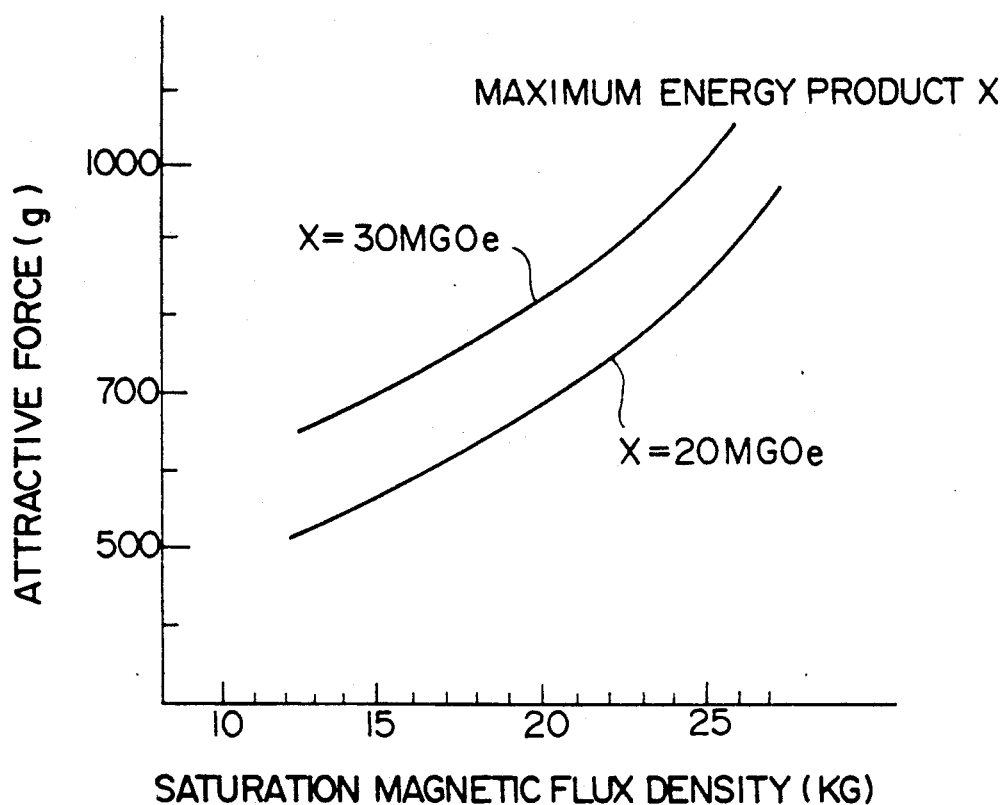
FIG. 5 is a diagram showing the relationship between the attractive force produced by a denture attachment and the saturation magnetic flux density of the end plate according to the present invention.
Figure 6:
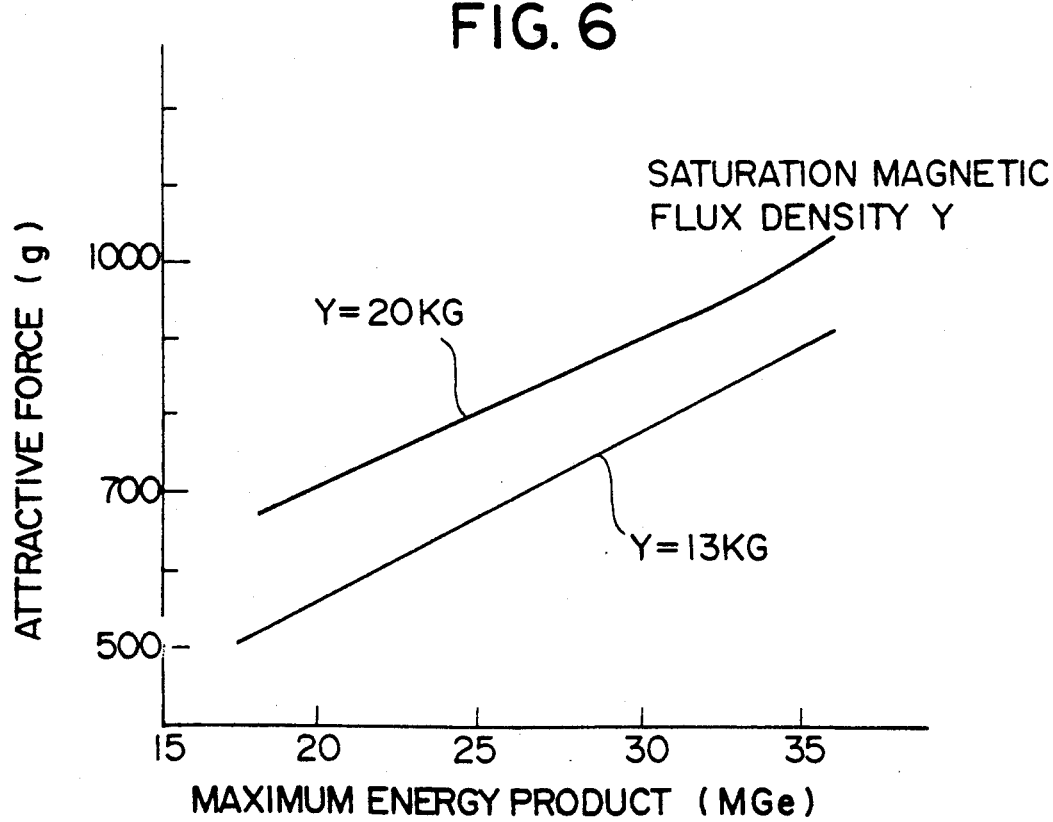
FIG. 6 is a diagram showing the relationship between the attractive force produced by a denture attachment and the maximum energy product of the magnet body according to the present invention.

In the attachment having the structure as described above, the attractive force is varied with variations in the saturation magnetic flux density of the soft magnetic alloy constituting the end plates and in the maximum energy product of the magnet body. This is shown in FIGS. 5 and 6. As seen from the two diagrams, it is possible to obtain a denture attachment having a high attractive force of 500 to 1000 g by selecting the two characteristics, namely, the saturation magnetic flux density and the maximum energy product.

According to the denture attachment of the present invention, it is possible to obtain a small denture attachment which, as mentioned above, has a strong attractive force between the attachment and the coping 93 as well as excellent corrosion resistance and wear resistance.

Now three kinds of denture attachment No. A1, No. A2 and No. A3 were produced according to the present invention, and the attractive force, corrosion resistance and wear resistance of the attachments were measured. As for structure, the attachments were each in a prismatic form substantially the same as that in FIG. 4. The shape, magnetic properties and material of the component members are set forth in Tables 1 to 3. The attachment No. A3 was plated with chromium (thickness: 10 μm) on the surface thereof facing the coping, on the surface of the end plates, the cap and the spacer. On the other hand, the attachments No. A1 and No. A2 were in the as-brazed condition.

The results of the measurements are given in Table 8.

As Comparative Examples I, attachments No. B1 and No. B2 having the same structure as the attachments according to the present invention were prepared by use of materials different in magnetic properties from the materials for the attachments according to the present invention, and subjected to the measurements. The shape and the like of the attachments No. B1 and No. B2 are given in Tables 4 and 5, and the measurement results shown in Table 8.

Figure 7:
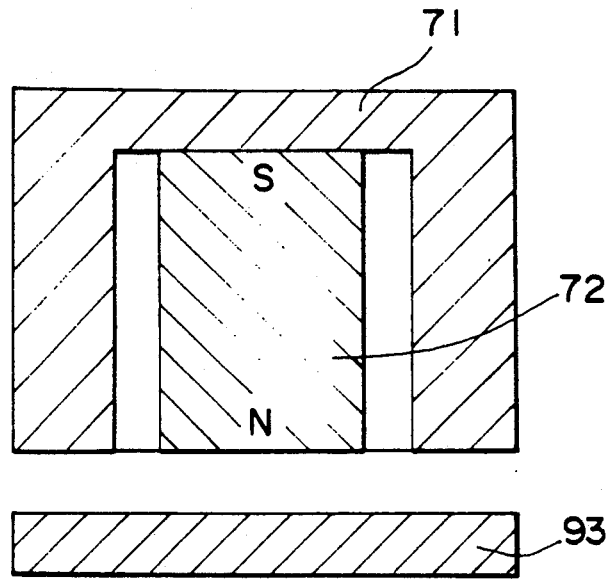
FIGS. 7 and 8 are each a sectional view of a comparative example in which a magnet body is disposed with the S-N direction set differently from that according to the present invention, by way of comparison.
Figure 8:
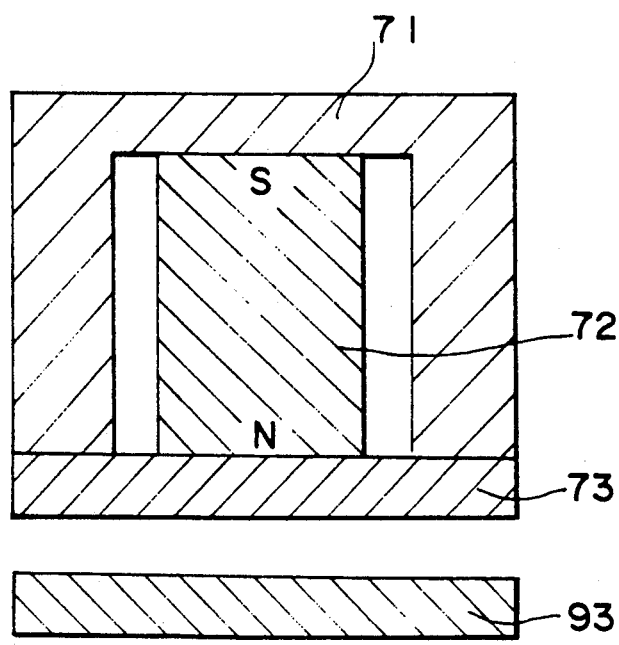

Further, as Comparative Examples II, attachments No. C1 and No. C2 different in both structure and material from the attachments according to the present invention were prepared, and subjected to the measurements. The shape and the like of the attachments No. C1 and No. C2 are set forth in Tables 6 and 7, and the measurement results in Table 8. The attachment No. C1 comprised, as shown in FIG. 7, an end plate 71 having an inverted U-shaped section, and a magnet body 72 disposed inside the end plate 71, with the S and N poles directed upward and downward, respectively. The magnet body 72 was placed in direct contact with the coping 93. The attachment No. C2 had a construction, as shown in FIG. 8, comprising a non-magnetic foil 73 additionally provided on the entire surface of the portion facing the coping 93 in the attachment No. C1.

The attractive force was measured in terms of the magnetic attractive force (g) between the attachment and the coping.

The corrosion resistance was evaluated based on the degree of discoloration of the attachment after immersion of the attachment in artificial saliva at 37° C. for 1000 hours. In Table 8, "O" represents "no discoloration" indicating superior corrosion resistance, while "X" represents "discoloration over entire surface", indicating poor corrosion resistance.

The wear resistance was evaluated based on the surface condition of the attachment after rubbing the coping and the attachment against each other 1000 times under a load of 1 kg per attachment. In the table, "O" represents "no change", indicating superior wear resistance, while "X" represents "damaged portion observed", indicating poor wear resistance. The area of contact of the coping with the attachment was 11 mm$^2$.

It is seen from Tables 1 to 8 that, as to corrosion resistance and wear resistance, the attachments Nos. A1 to A3 according to the present invention and the attachments Nos. B1 and B2 of Comparative Example I are excellent, whereas the attachments Nos. C1 and C2 of Comparative Example II are poor.

As for the attractive force, all the denture attachments Nos. A1 to A3 according to the present invention showed high values of at least 720 g, whereas the attachments Nos. B1 and B2 of Comparative Example I showed low values of about 450 g, and the attachments Nos. C1 and C2 of Comparative Example II showed very low values of about 200 to 300 g.

TABLE 1

(Example, No. A1)

| | Shape (mm) | | | Magnetic properties | | Material |
|---|---|---|---|---|---|---|
| Magnet body | Width 4.0 | Height 2.5 | Thickness 1.0 | Maximum energy product 30 MGOe | | Rare-earth permanent magnet $Sm_2$—$Co_{17}$ |
| End plate | Width 4.0 | Sectional area 3 mm$^2$ | Thickness 3.0 | Saturation magnetic flux density 17000 | Permeability 5000 | Soft magnetic alloy 13Cr—2Mo steel |
| Spacer | Width 4.0 | Height 0.5 | Thickness 1.0 | Permeability 1.02 | | Non-magnetic alloy 17Cr—12Ni—2Mo steel |
| Cap | | Thickness 0.1 | | Permeability 1.02 | | Non-magnetic alloy 17Cr—12Ni—2Mo steel |
| Coping | Thickness 0.7 | Sectional area 11mm$^2$ | | Saturation magnetic flux density 17000 | Permeability 5000 | Soft magnetic alloy 13Cr—2Mo steel |

TABLE 2

(Example, No. A2)

| | Shape (mm) | | | Magnetic properties | | Material |
|---|---|---|---|---|---|---|
| Magnet body | Width 4.0 | Height 2.5 | Thickness 1.0 | Maximum energy product 30 MGOe | | Rare-earth permanent magnet $Sm_2$—$Co_{17}$ |
| End plate | Width 4.0 | Sectional area 3 mm$^2$ | Thickness 3.0 | Saturation magnetic flux density 14000 | Permeability 4000 | Soft magnetic alloy 17Cr—2Mo steel |
| Spacer | Width 4.0 | Height 0.5 | Thickness 1.0 | Permeability 1.02 | | Non-magnetic alloy 17Cr—12Ni—2Mo steel |
| Cap | | Thickness 0.1 | | Permeability 1.02 | | Non-magnetic alloy 17Cr—12Ni—2Mo steel |
| Coping | Thickness 0.7 | Sectional area | | Saturation magnetic | Permeability | Soft magnetic alloy 17Cr—2Mo steel |

TABLE 2-continued (Example, No. A2)

| | Shape (mm) | Magnetic properties | Material |
|---|---|---|---|
| | 11 mm² | flux density 4000 14000 | |

TABLE 3

(Example, No. A3)

| | Shape (mm) | | | Magnetic properties | | Material |
|---|---|---|---|---|---|---|
| Magnet body | Width 4.0 | Height 2.5 | Thickness 1.0 | Maximum energy product 30 MGOe | | Rare-earth permanent magnet $Sm_2$—$Co_{17}$ |
| End plate | Width 4.0 | Sectional area 3 mm² | Thickness 3.0 | Saturation magnetic flux density 22000 | Permeability 6000 | Pure iron |
| Spacer | Width 4.0 | Height 0.5 | Thickness 1.0 | Permeability 1.02 | | Non-magnetic alloy 17Cr—12Ni—2Mo steel |
| Cap | | Thickness 0.1 | | Permeability 1.02 | | Non-magnetic alloy 17Cr—12Ni—2Mo steel |
| Coping | Thickness 0.7 | | Sectional area 11 mm² | Saturation magnetic flux density 14000 | Permeability 4000 | Soft magnetic alloy 17Cr—2Mo steel |

TABLE 4

(Comparative Example I, No. B1)

| | Shape (mm) | | | Magnetic properties | | Material |
|---|---|---|---|---|---|---|
| Magnet body | Width 4.0 | Height 2.5 | Thickness 1.0 | Maximum energy product 20 MGOe | | Rare-earth permanent magnet $Sm_2$—$Co_5$ |
| End plate | Width 4.0 | Sectional area 3 mm² | Thickness 3.0 | Saturation magnetic flux density 10000 | Permeability 1000 | Soft magnetic alloy 85Ni—15Fe |
| Spacer | Width 4.0 | Height 0.5 | Thickness 1.0 | Permeability 1.02 | | Non-magnetic alloy 17Cr—12Ni—2Mo steel |
| Cap | | Thickness 0.1 | | Permeability 1.02 | | Non-magnetic alloy 17Cr—12Ni—2Mo steel |
| Coping | Thickness 0.7 | | Sectional area 11 mm² | Saturation magnetic flux density 10000 | Permeability 1000 | Soft magnetic alloy 85Ni—15Fe |

TABLE 5

(Comparative Example I, No. B2)

| | Shape (mm) | | | Magnetic properties | | Material |
|---|---|---|---|---|---|---|
| Magnet body | Width 4.0 | Height 2.5 | Thickness 1.0 | Maximum energy product 15 MGOe | | Rare-earth permanent magnet Sm—$Co_5$ |
| End plate | Width 4.0 | Sectional area 3 mm² | Thickness 3.0 | Saturation magnetic flux density 14000 | Permeability 4000 | Soft magnetic alloy 17Cr—2Mo steel |
| Spacer | Width 4.0 | Height 0.5 | Thickness 1.0 | Permeability 1.02 | | Non-magnetic alloy 17Cr—12Ni—2Mo steel |
| Cap | | Thickness 0.1 | | Permeability 1.02 | | Non-magnetic alloy 17Cr—12Ni—2Mo steel |
| Coping | Thickness 0.7 | | Sectional area 11 mm² | Saturation magnetic flux density 14000 | Permeability 4000 | Soft magnetic alloy 17Cr—2Mo steel |

TABLE 6

(Comparative Example II, No. C1)

| | Shape (mm) | | | Magnetic properties | | Material |
|---|---|---|---|---|---|---|
| Magnet body | Width 4.0 | Height 2.5 | Thickness 1.0 | Maximum energy product 30 MGOe | | Rare-earth permanent magnet $Sm_2$—$Co_{17}$ |
| End plate | Width 4.0 | Sectional area 3 mm² | Thickness 3.0 | Saturation magnetic flux density 13000 | Permeability 4000 | Soft magnetic alloy 26Cr—1Mo steel |
| Coping | Thickness 0.7 | | Sectional area 11 mm² | Saturation magnetic flux density | Permeability 3000 | Soft magnetic alloy Pd—Co—Ni alloy |

TABLE 6-continued

| (Comparative Example II, No. C1) | | |
|---|---|---|
| Shape (mm) | Magnetic properties | Material |
| | 7500 | |

TABLE 7

| | (Comparative Example II, No. C2) | | | | |
|---|---|---|---|---|---|
| | Shape (mm) | | | Magnetic properties | Material |
| Magnet body | Width 4.0 | Height 2.5 | Thickness 1.0 | Maximum energy product 30 MGOe | Rare-earth permanent magnet $Sm_2$—$Co_{17}$ |
| End plate | Width 4.0 | Sectional area 3 mm$^2$ | Thickness 3.0 | Saturation magnetic flux density 13000 / Permeability 4000 | Soft magnetic alloy 26Cr—1Mo steel |
| Foil | Thickness 0.1 | | | Permeability 1.02 | Non-magnetic alloy 17Cr—12Ni—2Mo steel |
| Coping | Thickness 0.7 | Sectional area 11 mm$^2$ | | Saturation magnetic flux density 7500 / Permeability 3000 | Soft magnetic alloy Pd—Co—Ni alloy |

TABLE 8

| (Results of Measurements) | | | | | | | |
|---|---|---|---|---|---|---|---|
| | Example | | | Comparative Example I | | Compartive Example II | |
| | A1 | A2 | A3 | B1 | B2 | C1 | C2 |
| Attractive force (g) | 850 | 720 | 900 | 450 | 460 | 300 | 200 |
| Corrosion resistance (discoloration) | O | O | O | O | O | X | O |
| Wear Resistance | O | O | O | O | O | X | X |

WELDING OF JOINT PORTIONS OF DENTURE ATTACHMENT

For securing a sufficient rustproofing ability at the joint portions between the cap and both the end plates and the spacer as well as the joint portions between the end plates and the spacer in the denture attachment according to the present invention, joining by welding is preferable to joining by brazing or a cement. In the welding, sufficient depth of penetration between the members to be joined together is required. If the width of bead is increased, for a given depth of weld penetration at a joint portion, the magnetic properties of an end plate portion are degraded, and an increased input of welding heat lowers the corrosion resistance, causing a heavier mechanical strain. Thus it has been found necessary to minimize the width of bead while securing a sufficient depth of weld penetration at the joint portions. Based on the finding, the present invention provides a denture attachment of the above-mentioned type in which the joint portions between the cap and both the end plates and the spacer and the joint portions between the end plates and the spacer on the coping side are joined by laser welding or electron beam welding, over the entire length of each joint portion exposed to the surface of the attachment.

Besides, in the denture attachment according to the present invention, it is preferable that the depth of weld penetration at the joint portions is at least 0.02 mm and not more than the height of the spacer. If the depth of penetration is less than 0.02 mm, it is impossible to obtain sufficient strength at the joint portions, and it is also impossible to secure a satisfactory seal against saliva. On the other hand, if the depth of weld penetration is more than the height of the spacer, the thermal effect of welding is exerted on the magnet body to deteriorate the magnetic characteristics of the magnet body.

In the present invention, the height of the spacer is preferably 0.05 to 1.0 mm. If the spacer height is less than 0.05 mm, it is difficult to secure sufficient wear resistance, and it is impossible to obtain a sealing property or sufficient strength at the joint portions. If the spacer height exceeds 1.0 mm, on the other hand, the magnetic attractive force becomes insufficient.

The laser welding or electron beam welding used in the present invention can be carried out by a conventionally known method. The welding method may be, for example, one of those methods illustrated respectively by FIGS. 9a, 9b, 9c and 9d, among which the method of FIG. 9a yields the most satisfactory result. In FIGS. 9a to 9d, which each show a sectional view of a denture attachment, reference characters 20 and 20' each denotes a welded portion, and the same portions as those in FIG. 4 are denoted by the same reference characters as in FIG. 4.

As the magnet body, a rare-earth permanent magnet having a maximum energy product of at least 20 MGOe is preferably used. It is thereby possible to obtain a denture attachment having an attractive force of at least about 500 g. Examples of such a rare-earth permanent magnet include $Sm_2$ $Co_5$ or $SmCo_{17}$ alloys, Nd-Fe-B alloys, etc.

For higher corrosion resistance of the joint portions, it is preferable to use a corrosion-resistant soft magnetic alloy containing, by weight, up to 0.03% of C, 11 to 30% of Cr and up to 4% of Mo for the end plates, and Ti, a Ti alloy or a non-magnetic stainless steel containing up to 0.03% of C for the spacer and for the cap. If required, Nb or Ti may be added to the corrosion-resistant magnetic alloy.

In the denture attachment according to the present invention, the joint portions between the cap and both the end plates and the spacer as well as the joint portions between the end plates and the spacer are joined, with satisfactory mutual penetration of the materials of both adjacent members, by the laser welding or electron beam welding; as a result, the boundary surfaces are lost at the joint portions, enabling perfect prevention of the penetration of saliva. Thus, the magnet body is protected satisfactorily against the corrosion arising from penetration of saliva. In addition, the corrosion resistance of the joint portions becomes equivalent or superior to the corrosion resistance of the parent metals, so that there is no possibility of rusting or electrolytic corrosion proceeding from the joint portions.

Furthermore, the strength of the joint portions is higher, as compared with that in the case of brazing, so that the joint portions are free of the possibility of breaking due to mechanical stress or of wearing. In addition, the diameter of the weld spot is small, and the welding is instantaneously completed. There is therefore little effect of the welded zone on the end plates, and the welding does not cause deterioration in the magnetic characteristics or the attractive force. Moreover, the joint portions have excellent durability, and maintain stable corrosion resistance over a very long period, with no possibility of separation.

Now, some embodiments of the present invention will be explained together with comparative examples, to make clear advantageous the effects of the invention.

Figure 9A:
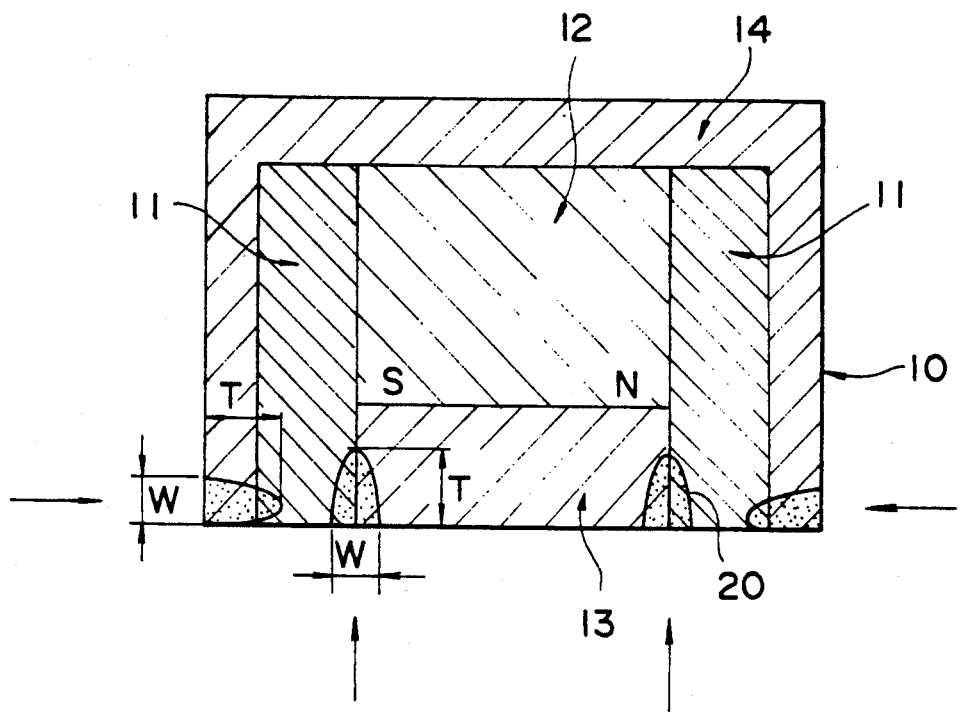
FIGS. 9a to 9d are each a sectional view for illustrating the welding positions in a denture attachment according to the present invention.
Figure 9B:
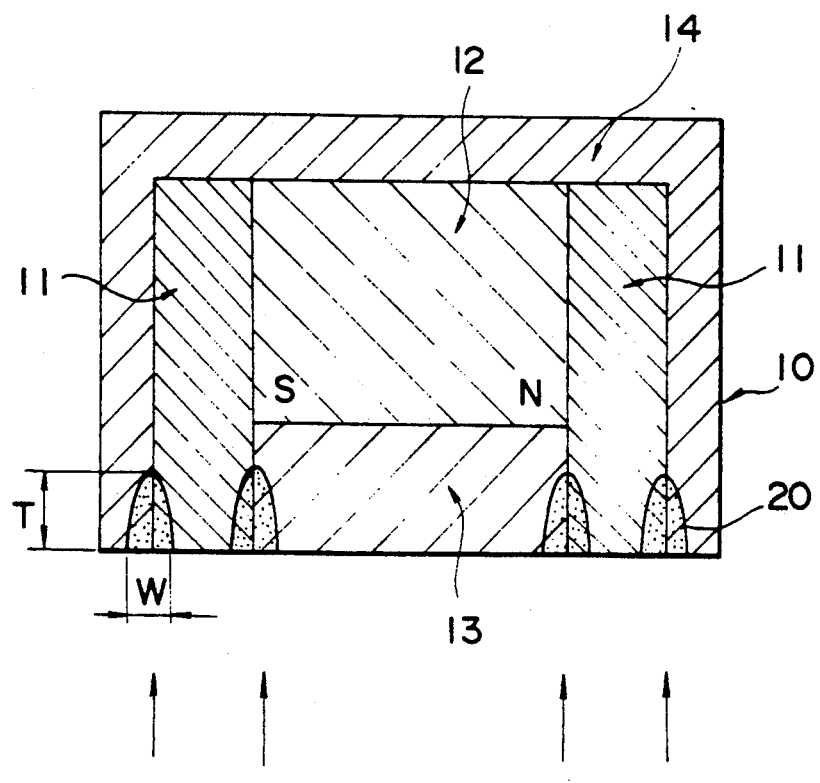
Figure 9C:
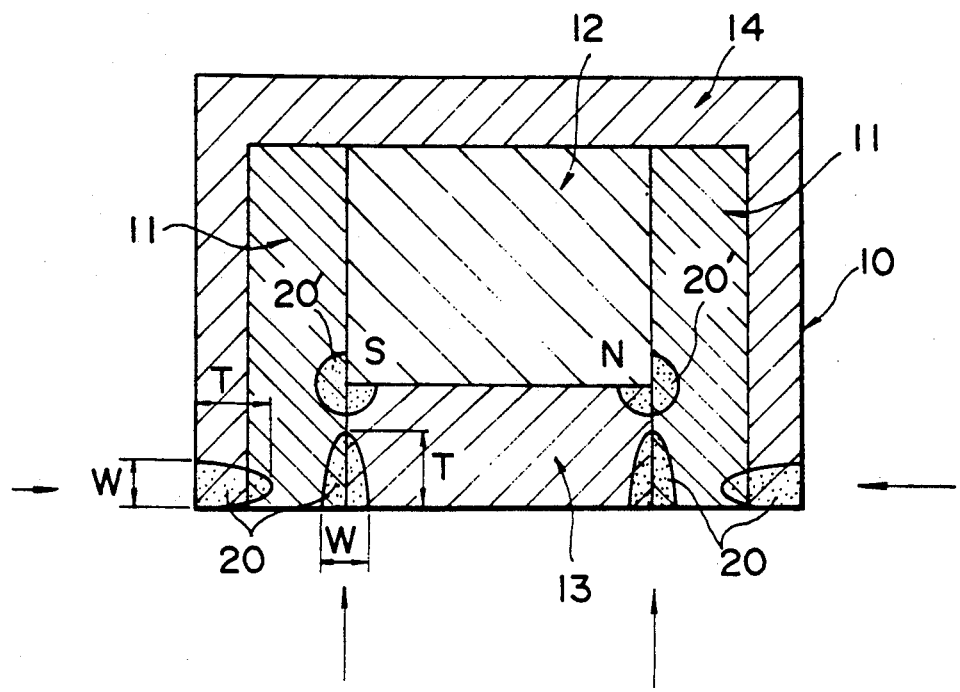
Figure 9D:
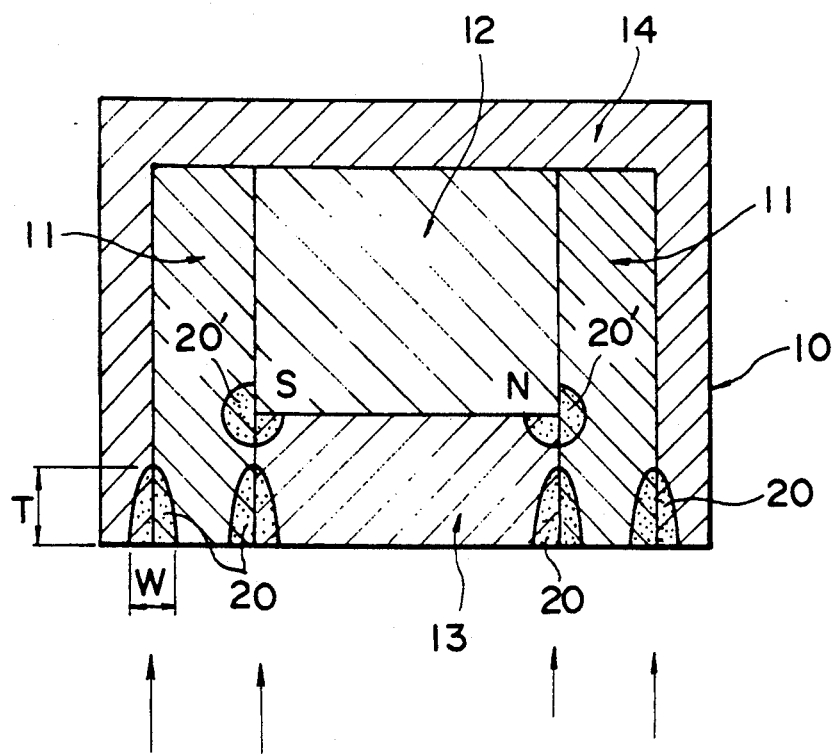

Denture attachments having the above-mentioned structure were prepared. First, as Examples of the present invention, four kinds of denture attachments based on respective combinations of dimensions of component parts, magnetic properties and materials as shown in Tables 9 to 12 were prepared by conducting laser welding by the welding method of FIG. 9a of FIG. 9b and with the bead shape shown in Table 19. In FIGS. 9a to 9d, the arrows each indicates the weld direction, W represents the width of bead, and T represents the depth of bead. The laser welding was carried out by use of a YAG laser in a pulsed oscillation mode, with a voltage of 250V and a pulse duration of 1.3 ms. In FIGS. 9c and 9d, the welds 20' are formed by welding from the side of the inner surfaces 111 of the end plates 11 after welding of the joint surfaces of the end faces 113 and 133 of the end plates 11 and the spacer 13, before the cap 14 and the magnet 12 are mounted.

Next, as the Comparative Examples III, denture attachments based on the respective combinations of dimensions of component members, the magnetic properties and materials given in Tables 13 and 14 were prepared. Joint portions were joined by use of a dental cement for No. B3 of Comparative Example III in Table 13, and by silver brazing for No. B4 of Comparative Example III in Table 14. By way of comparison, denture attachments as Comparative Examples IV were prepared by selecting the dimensions of component parts, the magnetic properties and the materials as given in Tables 15 to 18 and conducting laser welding by the welding method of FIGS. 9a or 9b with the bead shape given in Table 19.

TABLE 9

(Example, No. A4)

| | Shape (mm) | | | Magnetic properties | | Material |
|---|---|---|---|---|---|---|
| Magnet body | Width 4.0 | Height 2.5 | Thickness 1.0 | Maximum energy product 20 MGOe | | Rare-earth permanent magnet Sm—Co$_5$ |
| End plate | Width 4.0 | Sectional area 3 mm$^2$ | Thickness 3.0 | Saturation magnetic flux density 14000 | Permeability 4000 | Soft magnetic alloy 0.02C—17Cr—2Mo steel |
| Spacer | Width 4.0 | Height 0.5 | Thickness 1.0 | Permeability 1.02 | | Non-magnetic alloy 0.02C—Cr—12Ni—2Mo steel |
| Cap | | Thickness 0.1 | | Permeability 1.02 | | Non-magnetic alloy 0.02C—17Cr—12Ni—2Mo steel |
| Coping | Thickness 1.0 | Sectional area 11 mm$^2$ | | Saturation magnetic flux density 14000 | Permeability 4000 | Soft magnetic alloy 0.02C—17Cr—2Mo steel |

TABLE 10

(Example, No. A5)

| | Shape (mm) | | | Magnetic properties | | Material |
|---|---|---|---|---|---|---|
| Magnet body | Width 4.0 | Height 2.95 | Thickness 1.0 | Maximum energy product 20 MGOe | | Rare-earth permanent magnet Sm—Co$_5$ |
| End plate | Width 4.0 | Sectional area 3 mm$^2$ | Thickness 3.0 | Saturation magnetic flux density 14000 | Permeability 4000 | Soft magnetic alloy 0.02C—17Cr—2Mo steel |
| Spacer | Width 4.0 | Height 0.05 | Thickness 1.0 | Permeability 1.02 | | Non-magnetic alloy 0.02C—17Cr—12Ni—2Mo steel |
| Cap | | Thickness 0.1 | | Permeability 1.02 | | Non-magnetic alloy 0.02C—17Cr—12Ni—2Mo steel |
| Coping | Thickness 1.0 | Sectional area 11 mm$^2$ | | Saturation magnetic flux density 14000 | Permeability 4000 | Soft magnetic alloy 0.02C—17Cr—2Mo steel |

TABLE 11

(Example, No. A6)

| | Shape (mm) | | | Magnetic properties | | Material |
|---|---|---|---|---|---|---|
| Magnet body | Width 4.0 | Height 2.2 | Thickness 1.0 | Maximum energy product 20 MGOe | | Rare-earth permanent magnet Sm—Co$_5$ |
| End plate | Width 4.0 | Sectional area 3 mm$^2$ | Thickness 3.0 | Saturation magnetic flux density 14000 | Permeability 4000 | Soft magnetic alloy 0.02C—17Cr—2Mo steel |

TABLE 11-continued (Example, No. A6)

| | Shape (mm) | | | Magnetic properties | | Material |
|---|---|---|---|---|---|---|
| Spacer | Width 4.0 | Height 0.8 | Thickness 1.0 | Permeability 1.02 | | Non-magnetic alloy 0.02C—17Cr—12Ni—2Mo steel |
| Cap | | Thickness 0.1 | | Permeability 1.02 | | Non-magnetic alloy 0.02C—17Cr—12Ni—2Mo steel |
| Coping | Thickness 1.0 | Sectional area 11 mm$^2$ | | Saturation magnetic flux density 14000 | Permeability 4000 | Soft magnetic alloy 0.02C—17Cr—2Mo steel |

TABLE 12

(Example, No. A7)

| | Shape (mm) | | | Magnetic properties | | Material |
|---|---|---|---|---|---|---|
| Magnet body | Width 4.0 | Height 2.5 | Thickness 1.0 | Maximum energy product 20 MGOe | | Rare-earth permanent magnet Sm—Co$_5$ |
| End plate | Width 4.0 | Sectional area 3 mm$^2$ | Thickness 3.0 | Saturation magnetic flux density 14000 | Permeability 4000 | Soft magnetic alloy 0.02C—22Cr—2Mo—Ti steel |
| Spacer | Width 4.0 | Height 0.5 | Thickness 1.0 | Permeability 1.02 | | Non-magnetic alloy 0.02C—17Cr—12Ni—2Mo steel |
| Cap | | Thickness 0.1 | | Permeability 1.02 | | Non-magnetic alloy 0.02C—17Cr—12Ni—2Mo steel |
| Coping | Thickness 1.0 | Sectional area 11 mm$^2$ | | Saturation magnetic flux density 14000 | Permeability 4000 | Soft magnetic alloy 0.02C—22Cr—2Mo—0.1 Ti steel |

TABLE 13

(Comparative Example III, No. B3: joined by dental cement)

| | Shape (mm) | | | Magnetic properties | | Material |
|---|---|---|---|---|---|---|
| Magnet body | Width 4.0 | Height 2.5 | Thickness 1.0 | Maximum energy product 20 MGOe | | Rare-earth permanent magnet Sm—Co$_5$ |
| End plate | Width 4.0 | Sectional area 3 mm$^2$ | Thickness 3.0 | Saturation magnetic flux density 14000 | Permeability 4000 | Soft magnetic alloy 17Cr—2Mo steel |
| Spacer | Width 4.0 | Height 0.5 | Thickness 1.0 | Permeability 1.02 | | Non-magnetic alloy 17Cr—12Ni—2Mo steel |
| Cap | | Thickness 0.1 | | Permeability 1.02 | | Non-magnetic alloy 17Cr—12Ni—2Mo steel |
| Coping | Thickness 1.0 | Sectional area 11 mm$^2$ | | Saturation magnetic flux density 14000 | Permeability 4000 | Soft magnetic alloy 17 Cr—2Mo steel |

TABLE 14

(Comparative Example III, No. B4: joined by silver brazing)

| | Shape (mm) | | | Magnetic properties | | Material |
|---|---|---|---|---|---|---|
| Magnet body | Width 4.0 | Height 2.5 | Thickness 1.0 | Maximum energy product 20 MGOe | | Rare-earth permanent magnet Sm—Co$_5$ |
| End plate | Width 4.0 | Sectional area 3 mm$^2$ | Thickness 3.0 | Saturation magnetic flux density 14000 | Permeability 4000 | Soft magnetic alloy 17Cr—2Mo steel |
| Spacer | Width 4.0 | Height 0.5 | Thickness 1.0 | Permeability 1.02 | | Non-magnetic alloy 17Cr—12Ni—2Mo steel |
| Cap | | Thickness 0.1 | | Permeability 1.02 | | Non-magnetic alloy 17Cr—12Ni—2Mo steel |
| Coping | Thickness 1.0 | Sectional area 11 mm$^2$ | | Saturation magnetic flux density 14000 | Permeability 4000 | Soft magnetic alloy 17Cr—2Mo steel |

TABLE 15

(Comparative Example IV, No. B5)

| | Shape (mm) | | | Magnetic properties | | Material |
|---|---|---|---|---|---|---|
| Magnet body | Width 4.0 | Height 2.5 | Thickness 1.0 | Maximum energy product 20 MGOe | | Rare-earth permanent magnet Sm—Co$_5$ |
| End | Width | Sectional | Thickness | Saturation | Permea- | Soft magnetic alloy |

TABLE 15-continued (Comparative Example IV, No. B5)

| | Shape (mm) | | | Magnetic properties | | Material |
|---|---|---|---|---|---|---|
| plate | 4.0 | area 3 mm$^2$ | 3.0 | magnetic flux density 14000 | bility 4000 | 0.04C—17Cr—2Mo steel |
| Spacer | Width 4.0 | Height 0.5 | Thickness 1.0 | Permeability 1.02 | | Non-magnetic alloy 17Cr—12Ni—2Mo steel |
| Cap | | Thickness 0.1 | | Permeability 1.02 | | Non-magnetic alloy 17Cr—12Ni—2Mo steel |
| Coping | Thickness 1.0 | | Sectional area 11 mm$^2$ | Saturation magnetic flux density 14000 | Permeability 4000 | Soft magnetic alloy 17Cr—2Mo steel |

TABLE 16

(Comparative Example IV, No. B6)

| | Shape (mm) | | | Magnetic properties | | Material |
|---|---|---|---|---|---|---|
| Magnet body | Width 4.0 | Height 2.5 | Thickness 1.0 | Maximum energy product 20 MGOe | | Rare-earth permanent magnet Sm—Co$_5$ |
| End plate | Width 4.0 | Sectional area 3 mm$^2$ | Thickness 3.0 | Saturation magnetic flux density 14000 | Permeability 4000 | Soft magnetic alloy 0.02C—17Cr—2Mo steel |
| Spacer | Width 4.0 | Height 0.5 | Thickness 1.0 | Permeability 1.02 | | Non-magnetic alloy 0.02C—17Cr—12Ni—2Mo steel |
| Cap | | Thickness 0.1 | | Permeability 1.02 | | Non-magnetic alloy 0.02C—17Cr—12Ni—2Mo steel |
| Coping | Thickness 1.0 | | Sectional area 11 mm$^2$ | Saturation magnetic flux density 14000 | Permeability 4000 | Soft magnetic alloy 0.02C—17Cr—2Mo steel |

TABLE 17

(Comparative Example, IV, No. B7)

| | Shape (mm) | | | Magnetic properties | | Material |
|---|---|---|---|---|---|---|
| Magnet body | Width 4.0 | Height 2.98 | Thickness 1.0 | Maximum energy product 20 MGOe | | Rare-earth permanent magnet Sm—Co$_5$ |
| End plate | Width 4.0 | Sectional area 3 mm$^2$ | Thickness 3.0 | Saturation magnetic flux density 14000 | Permeability 4000 | Soft magnetic alloy 0.02C—17Cr—2Mo steel |
| Spacer | Width 4.0 | Height 0.02 | Thickness 1.0 | Permeability 1.02 | | Non-magnetic alloy 0.02C—17Cr—12Ni—2Mo steel |
| Cap | | Thickness 0.1 | | Permeability 1.02 | | Non-magnetic alloy 0.02C—17Cr—12Ni—2Mo steel |
| Coping | Thickness 1.0 | | Sectional area 11 mm$^2$ | Saturation magnetic flux density 14000 | Permeability 4000 | Soft magnetic alloy 0.02C—17Cr—2Mo steel |

TABLE 18

(Comparative Example, IV, No. B8)

| | Shape (mm) | | | Magnetic properties | | Material |
|---|---|---|---|---|---|---|
| Magnet body | Width 4.0 | Height 2.5 | Thickness 1.0 | Maximum energy product 20 MGOe | | Rare-earth permanent magnet Sm—Co$_5$ |
| End plate | Width 4.0 | Sectional area 3 mm$^2$ | Thickness 3.0 | Saturation magnetic flux density 14000 | Permeability 4000 | Soft magnetic alloy 17Cr—2Mo steel |
| Spacer | Width 4.0 | Height 0.5 | Thickness 1.0 | Permeability 1.02 | | Non-magnetic alloy 0.04C—17Cr—12Ni—2Mo steel |
| Cap | | Thickness 0.1 | | Permeability 1.02 | | Non-magnetic alloy 0.04C—17Cr—12Ni—2Mo steel |
| Coping | Thickness 1.0 | | Sectional area 11 mm$^2$ | Saturation magnetic flux density 14000 | Permeability 4000 | Soft magnetic alloy 17Cr—2Mo steel |

TABLE 19

| | | | Welding Method and Bead Shape (mm) | | | | | | | |
|---|---|---|---|---|---|---|---|---|---|---|
| | | | Example | | | | Comparative Example IV | | | |
| | | | No. A4 | No. A5 | No. A6 | No. A7 | No. B5 | No. B6 | No. B7 | No. B8 |
| Welding Method | | | (a) | (b) | (a) | (a) | (a) | (a) | (b) | (a) |
| Shape | Weld of Cap | Width (W) | 0.03 | 0.03 | 0.50 | 0.40 | 0.30 | 1.00 | 0.22 | 0.30 |
| | | Depth (T) | 0.20 | 0.02 | 0.30 | 0.30 | 0.20 | 0.60 | 0.01 | 0.20 |
| | Weld of Spacer | Width (W) | 0.30 | 0.03 | 0.60 | 0.35 | 0.30 | 0.50 | 0.02 | 0.30 |
| | | Depth (T) | 0.20 | 0.02 | 0.40 | 0.30 | 0.20 | 0.35 | 0.01 | 0.20 |
| Height of Spacer | | | 0.5 | 0.05 | 0.8 | 0.5 | 0.5 | 0.5 | 0.02 | 0.5 |

The denture attachments prepared as Examples, Comparative Examples III and Comparative Examples IV in the manner described above were subjected to measurement of sealing property, corrosion resistance, wear resistance, strength of joint portion, and attractive force. The results are set forth in Table 20.

The sealing property was evaluated by immersing the denture attachment in water for 20 days, and splitting the attachment to inspect the inside condition. The specimens not rusted due to penetration of water are marked O, whereas the specimens rusted are marked X.

Corrosion resistance was evaluated based on the degree of discoloration of the denture attachment after immersion in artificial saliva at 37° C. for 1000 hours and for 5000 hours. The specimens not discolored are marked O, and the specimens showing a discoloration are marked X. Though the applicability of the denture attachment to ordinary clinical use can be judged from the results of a 1000-hour corrosion test, a test under the further severer condition of 5000-hour immersion was also carried out.

Wear resistance was evaluated by observing the surface condition of the denture attachment after rubbing the coping and the attachment against each other, 1000 times and 5000 times, under a load of 1 kg per attachment. The specimens not showing any change, because of the excellent wear resistance thereof, are marked O, whereas the specimens showing a damaged portion are marked X.

The strength of joint portion were evaluated by observing the condition of the joint portion after the denture attachment was compressed under a load of 100 kg per attachment. The specimens of which the joined members were not separated are marked O, and the specimens showing separation at the joint portion are marked X.

The attractive force was determined in terms of the magnetic attractive force (g) between the denture attachment and the coping.

As seen from the measurement results set forth in Table 20, No. B3 of Comparative Example III shown in Table 13 and No. B4 of Comparative Example III shown in Table 14, having the joint portions joined by a dental cement and by silver brazing, respectively, are unsatisfactory in strength of the joint portions and in corrosion resistance under severe conditions.

No. B5 of Comparative Example IV shown in Table 15, in which the material of the end plates has a high C content of 0.04%, is poor in corrosion resistance. No. B6 of Comparative Example IV shown in Table 16, in which the width of bead at the weld of the cap, 1.00 mm, is greater than the height of the spacer as shown in Table 19, shows a markedly lowered attractive force due to the effect of the welding heat on the magnet body. No. B7 of Comparative Example IV shown in Table 17, having a small spacer height of 0.02 mm, is poor in wear resistance and is therefore unsatisfactory in sealing properties and the strength of the joint portions. No. B8 of Comparative Example IV shown in Table 18, in which the cap material has a high C content of 0.04%, is poor in corrosion resistance.

Examples of the present invention, Nos. A4 to A7 shown in Tables 9 to 12, in which the boundary surfaces of end plates, cap and spacer on the coping side are joined by laser welding, are excellent in sealing property, corrosion resistance, wear resistance and the strength of joint portions, and have a high attractive force of 700 to 900 g. Thus, the effect of the welding according to the present invention is confirmed.

As has been described above, the denture attachment according to the present invention comprises a magnet body of a rare-earth permanent magnet disposed between a pair of end plates perpendicular to a coping, a spacer of a non-magnetic alloy disposed beneath the magnet body, and a cap covering entirely these component members of the attachment, except on the coping side of the end plates and spacer, and, when the joining of the boundary surfaces of the cap, end plates and spacer on the coping side is made by laser welding or electron beam welding, the joint portions are fused so as

TABLE 20

| | Example | | | | Comparative Example III | | Comparative Example IV | | | |
|---|---|---|---|---|---|---|---|---|---|---|
| | No. A4 | No. A5 | No. A6 | No. A7 | No. B3 | No. B4 | No. B5 | No. B6 | No. B7 | No. B8 |
| Sealing Proprty | | | | | | | | | X | |
| Corrosion Resistance 5000 hr | | | | | X | X | X | | | X |
| Wear Resistance | | | | | | | | | X | |
| Strength of Joint Portion | | | | | X | X | | | X | X |
| Attractive Force | 800 | 900 | 700 | 730 | 750 | 650 | 770 | 410 | 890 | 790 |
| Corrosion Resistance 1000 hr | | | | | | | X | | | X | to eliminate completely the boundary portions of the members. As a result, satisfactory waterproofing property is obtained, and the magnet body is protected from corrosion. In addition, the joint portions have excellent corrosion resistance, sufficient strength and high wear resistance. The magnetic characteristics of the members of the attachment are little affected by the welding of the joint portions. Thus, the magnetic characteristics are not deteriorated, and a high magnetic attractive force is secured. Moreover, the joint portions are durable, and the corrosion resistance is maintained for a long time.

AUGMENTATION OF MAGNETIC ATTRACTIVE FORCE OF DENTURE ATTACHMENT

Figure 10:
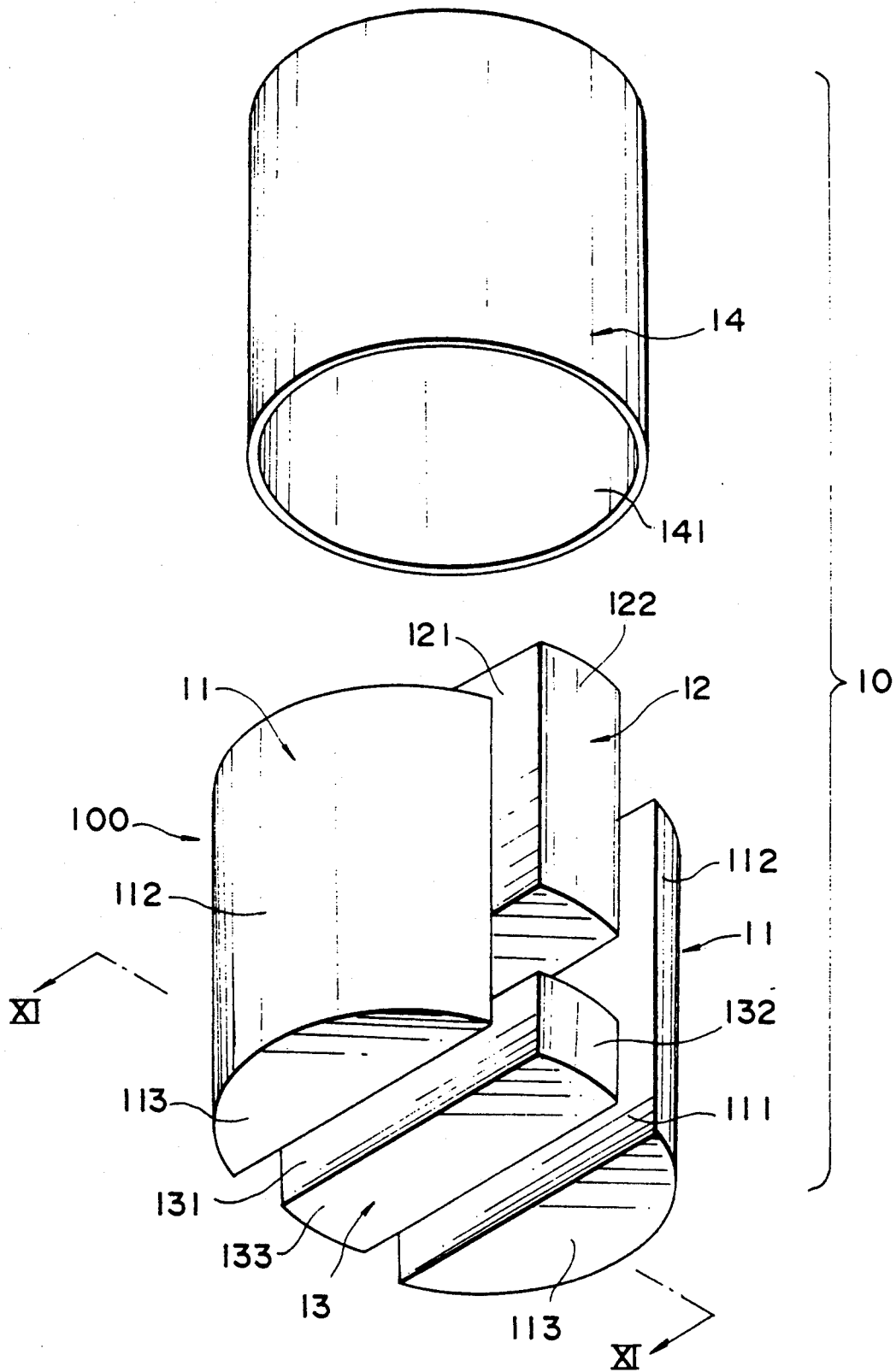
FIG. 10 is an exploded perspective view of another embodiment of the denture attachment according to the present invention.
Figure 11:
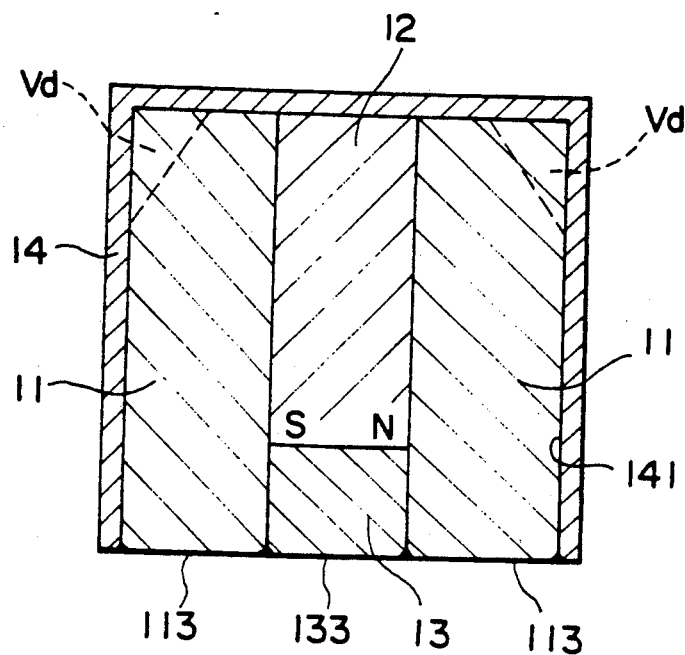
FIG. 11 is a sectional view taken along line XI—XI of FIG. 10.

FIGS. 10 and 11 illustrates another embodiment of the denture attachment according to the present invention. In the embodiment, outer peripheral surfaces 112, 112 of end plates 11, 11 are formed as cylindrical surfaces, and second side surfaces 122, 132 of a magnet 12 and a spacer 13 are formed as cylindrical surfaces for smooth continuity with the outer peripheral surfaces 112, 112 of the end plates 11, 11. In another structural points, the embodiment is the same as the embodiment shown in FIGS. 3 and 4.

Figure 12:
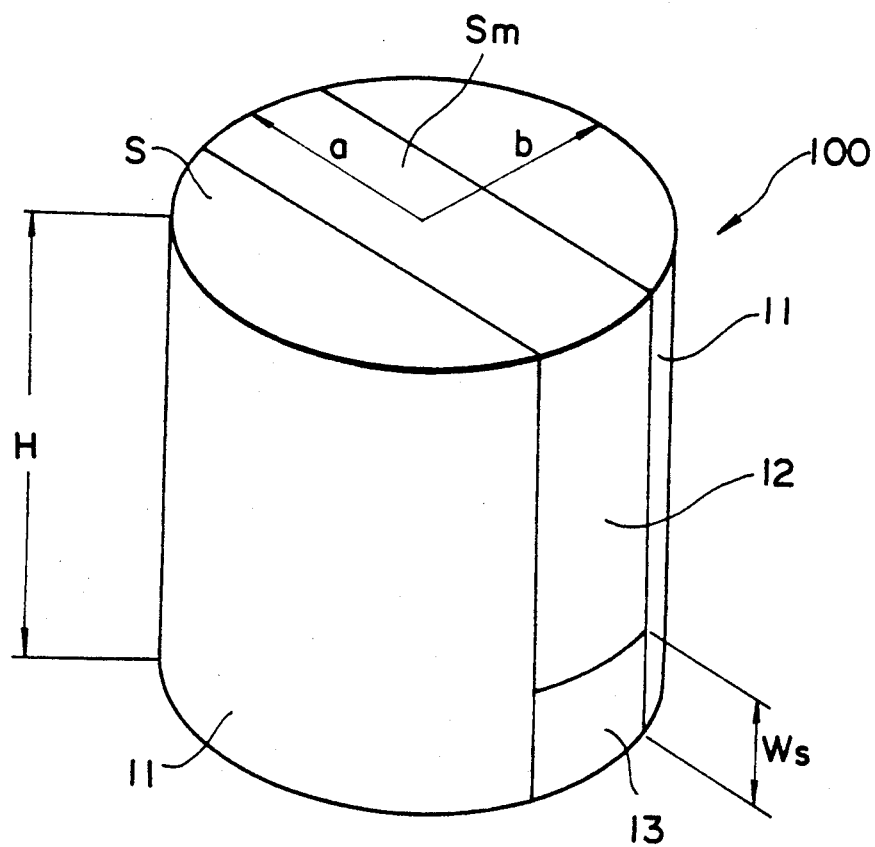
FIG. 12 is a perspective view for illustrating the dimensions of each portion of a denture attachment main body.

FIG. 12 shows a joined assembly of the pair of end plates 11, 11, the magnet body 12 and the spacer 13, which assembly constitutes the denture attachment together with a cap 14. Here, the joined assembly is referred to as the denture attachment main body 100. In the denture attachment main body 100 according to this embodiment, the section along a plane perpendicular to the height direction of the end plates 11 has an elliptic shape with the minor diameter in the direction of connecting the pair of end plates 11.

When the shape, magnetic properties and material of each component members of the denture attachment main body 100 are as set forth in Table 2 as Example No. A2, the volume V of the denture attachment main body is 30.0 mm³, while the magnetic attractive force F is 720 g, and the magnetic attractive force per unit volume, F/V, is therefore 24 g/mm³.

However, in the denture attachment using the denture attachment main body 100 having the above-mentioned dimensional values, the volume of the main body is large and the magnetic attractive force per unit volume is not always satisfactory.

Figure 13:
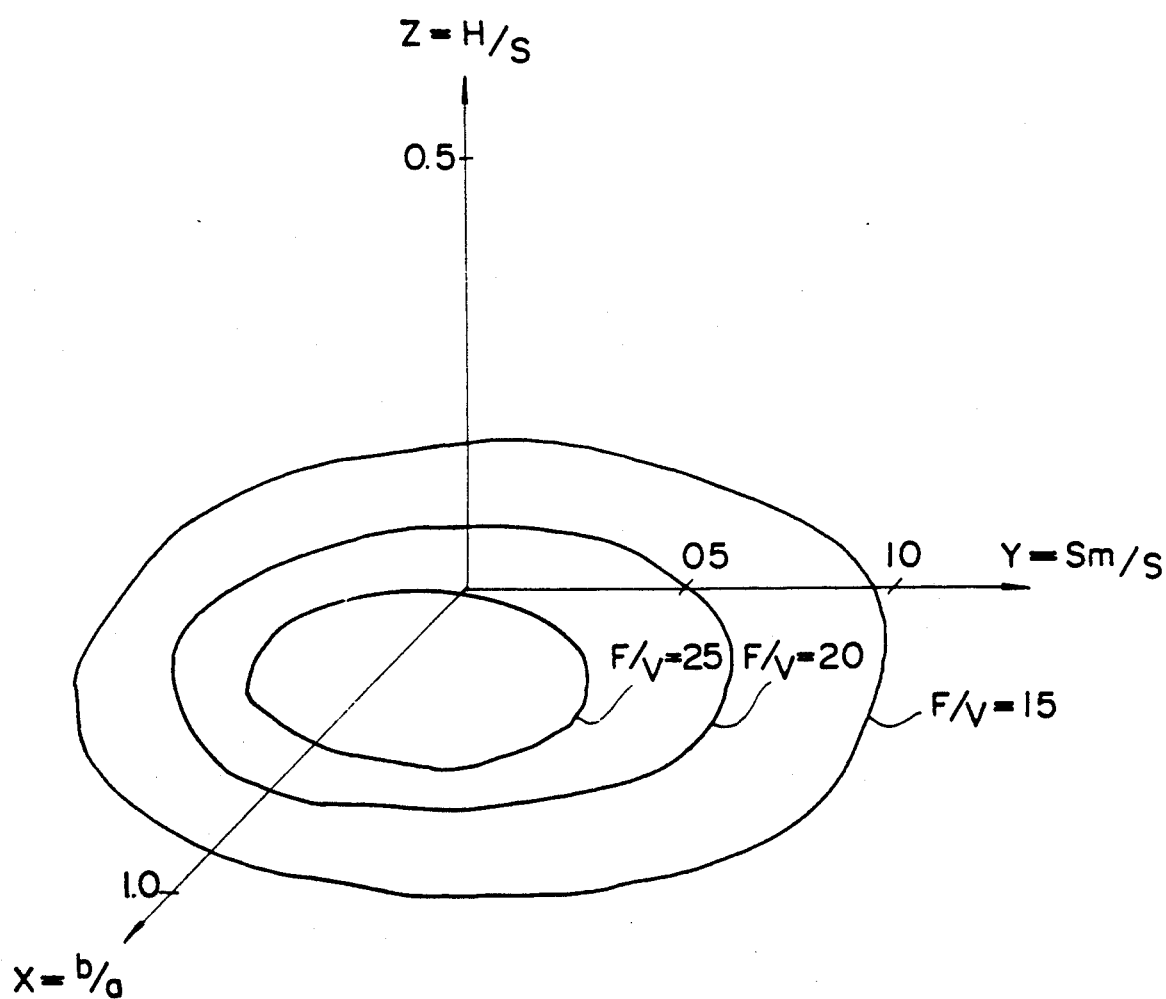
FIG. 13 is a diagram showing the relationship between the dimensions of the denture attachment main body and the magnetic attractive force per unit volume, F/V.

The present inventors arranged dimensional values of the denture attachment main body 100 shown in FIG. 12 into three factors, X=b/a, Y=SM/S and Z=H/S, and made intensive studies of the relationship between the three factors and the magnetic attractive force per unit volume, F/V. As a result of the studies it was found that, as appearing as an ellipsoidal spherical region in FIG. 13, a region of F/V≧25 where the dimensional values are so set as that the factors $X=b/a$, $Y=SM/S$, and $Z=H/S$ where 'H: height (mm) of denture attachment main body S: cross-sectional area (mm²) of denture attachment main body, a: major radius (mm) of denture attachment main body, b: minor radius (mm) of denture attachment main body, and Sm: cross-sectional area (mm²) of magnet body, satisfy the following inequality:

$$\frac{(X-0.75)^2}{0.25^2} + \frac{(Y-0.4)^2}{0.35^2} + \frac{(Z-0.15)^2}{0.1^2} \leq 1.$$

Figure 14:
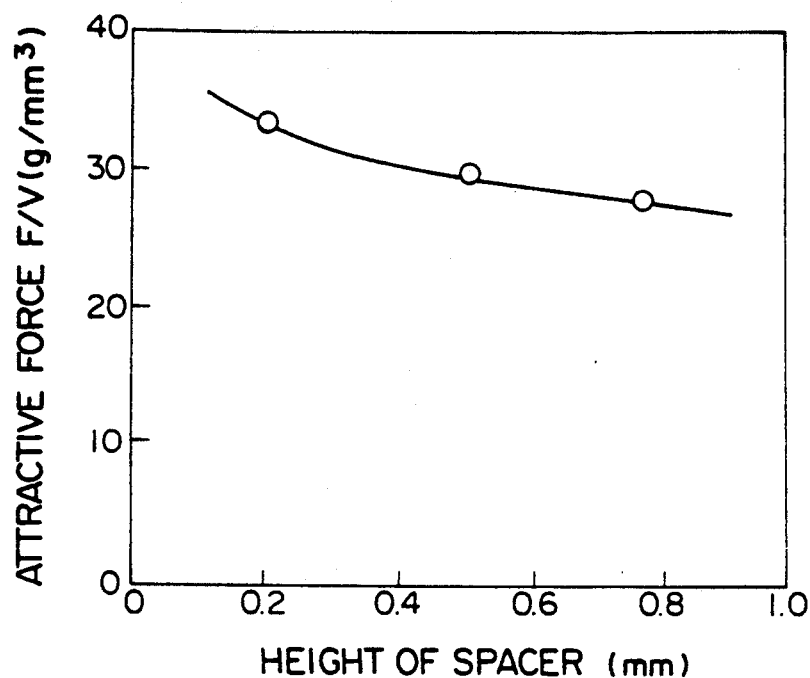
FIG. 14 is a diagram showing the relationship between the thickness of a spacer and the magnetic attractive force per unit volume, F/V.

Meanwhile, FIG. 14 is a diagram showing the relationship between the height of the spacer and F/V. As seen from the diagram, for obtaining the relationship F/V≧25 it is preferably to set the spacer height in the range of 0.05 to 1.0 mm, in the denture attachment which satisfies the above inequality.

Figure 15:
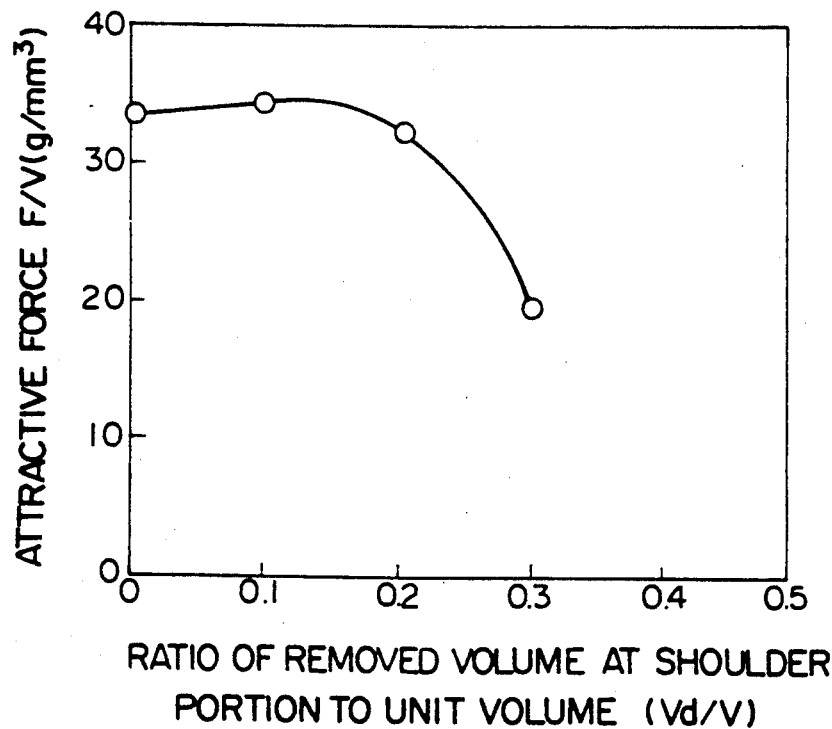
FIG. 15 is a diagram showing the relationship between the volume ratio Vd/V in which a volume Vd of a shoulder portion of an end plate removed and the original volume V of the end plate, and the attractive force per unit volume, F/V.

FIG. 15 is a diagram showing the relationship between the volume Vd of removal of shoulder portion of the end plate having no effect on formation of the magnetic circuit, and F/V. It is seen from the diagram that, for obtaining the relationship F/V≧25, it is preferable to set the ratio Vd/V of the volume Vd of the shoulder portion removed to the volume V of the denture attachment main body in the range of not more than 0.25.

Besides, it is preferable to use a magnet having a maximum energy of at least 20 MGOe for the magnet body in the denture attachment according to the present invention, and a magnet having a saturation magnetic flux density of at least 13,000 g for the end plates. In addition, it is preferably that the thickness of the coping is not more than 1.5 mm and the thickness of the cap is not more than 0.3 mm.

The denture attachment of the present invention has such dimensional values that the factors X=b/a, Y=SM/S and Z=H/S satisfy the following inequality:

$$\frac{(X-0.75)^2}{0.25^2} + \frac{(Y-0.4)^2}{0.35^2} + \frac{(Z-0.15)^2}{0.1^2} \leq 1,$$

whereby the relationship F/V≧25 is fulfilled, and, accordingly, the magnetic force per unit volume, F/V, is enhanced from the conventional value of 24 g/mm³ to a value ranging from 25 to 35 g/mm³.

The above-mentioned setting of the dimensional values makes it also possible to reduce the volume of the denture attachment main body from a value of 30 mm³ to a value of not more than 25 mm³.

Some preferred embodiments of the present invention will now be explained below together with comparative examples, thereby making clear the advantageous effects of the present invention.

As Examples of the present invention, denture attachments having the dimensional values of the component members as specified by the present invention, as shown in Table 22, were prepared by using materials having the magnetic properties shown in Table 21 for the magnet body, end plates, spacer and coping. As Comparative Examples V, denture attachments having the dimensional values of the component members outside ranges specified by the present invention, as set forth in Table 23, were produced. In Tables 22 and 23, f (X, Y, Z) represents the value of the left-hand expression of the above-mentioned inequality.

For the denture attachments prepared as Examples of the present invention and the denture attachments prepared as Comparative Examples, the magnetic attractive force F and the volume V were measured, and the magnetic attractive force per unit volume, F/V, was calculated. Also, the denture attachments were subjected to measurement of corrosion resistance, durability and wear resistance. The results obtained are set forth in Tables 24 and 25.

Corrosion resistance was evaluated in terms of the degree of discoloration of the denture attachment after immersion in artificial saliva (0.05% HCl) at 37° C. for 1000 hours. The specimens not discolored are marked O, while the specimens showing a discoloration are marked X.

Wear resistance was evaluated by observing the surface condition of the denture attachment after rubbing the coping and the denture attachment against each other 1000 times under a load of 1 kg per attachment. The specimens not showing any change, because of the excellent wear resistance thereof, are marked O, and the specimens showing a damaged portion are marked X.

Though 17Cr-2Mo steel was used as the end plate material in these embodiments, it was confirmed that the equivalent results are also obtainable by use of highly corrosion-resistant soft magnetic alloy having a saturation magnetic flux density of at least 13,000 and a permeability of at least 3000, such as 13Cr stainless steel, 26Cr stainless steel etc.

TABLE 21

| | Magnetic properties | | Material |
|---|---|---|---|
| Magnet body | Maximum energy product: | 20 MGOe | Rare-earth permanent magnet Sm—Co$_{17}$ |
| End plate | Saturation magnetic flux density: Permeability: | 14000 G 4000 | Soft magnetic alloy 17Cr—2Mo steel |
| Spacer | Permeability: | 1.02 | Non-magnetic alloy 17Cr—12Ni—2Mo steel |
| Coping | Saturation magnetic flux density: Permeability: | 14000 G 4000 | Soft magnetic alloy 17Cr—2Mo steel |

TABLE 22

| | (Examples) | | | | | | | | |
|---|---|---|---|---|---|---|---|---|---|
| No. | A8 | A9 | A10 | A11 | A12 | A13 | A14 | A15 | A16 |
| Height of Main Body H (mm) | 2.0 | 2.0 | 2.5 | 1.5 | 2.0 | 1.5 | 1.8 | 2.0 | 2.0 |
| Cross-sectional Area of Main Body S(mm$^2$) | 10 | 10 | 10 | 10 | 15 | 18 | 12 | 12 | 10 |
| Cross-sectional Area of Magnet Body Sm(mm$^2$) | 4.0 | 4.0 | 4.0 | 4.0 | 3.2 | 4.0 | 4.8 | 1.2 | 4.0 |
| Thickness of Spacer Ws(mm) | 0.2 | 0.3 | 0.2 | 0.2 | 0.5 | 0.2 | 0.2 | 0.2 | 0.2 |
| Thickness of Coping Wk(mm) | 1.0 | 1.0 | 0.7 | 1.0 | 1.0 | 1.0 | 1.0 | 0.5 | 1.0 |
| Volume of Shoulder Portion Removed Vd(mm$^3$) | 0 | 0 | 0 | 0 | 0 | 0 | 0 | 0 | 2.0 |
| Major Radius-Minor Radius Ratio b/a | 0.75 | 0.65 | 0.75 | 0.75 | 0.75 | 0.65 | 1.0 | 0.75 | 0.75 |
| Sm/S | 0.4 | 0.4 | 0.4 | 0.4 | 0.21 | 0.22 | 0.4 | 0.1 | 0.4 |
| H/S | 0.2 | 0.2 | 0.25 | 0.15 | 0.13 | 0.08 | 0.15 | 0.17 | 0.2 |
| Volume of Main Body V(mm$^3$) | 20 | 20 | 25 | 15 | 30 | 27 | 21.6 | 30 | 20 |
| Vd/V | 0 | 0 | 0 | 0 | 0 | 0 | 0 | 0 | 0.1 |
| f(X, Y, Z) | 0.25 | 0.41 | 1.0 | 0 | 0.33 | 0.91 | 1.0 | 0.77 | 0.25 |

TABLE 23

| | (Comparative Examples V) | | | | | | |
|---|---|---|---|---|---|---|---|
| No. | B9 | B10 | B11 | B12 | B13 | B14 | B15 |
| Height of Main Body H(mm) | 3.0 | 3.0 | 3.0 | 3.0 | 3.0 | 3.5 | 2.5 |
| Cross-sectional Area of Main Body S(mm$^2$) | 10 | 10 | 10 | 10 | 10 | 10 | 10 |
| Cross-sectional Area of Magnet Body Sm(mm$^2$) | 4.0 | 4.0 | 4.0 | 8.0 | 0.5 | 6.0 | 6.0 |
| Height of Spacer Ws(mm) | 0.5 | 0.05 | 0.5 | 0.2 | 0.3 | 0.5 | 0.5 |
| Thickness of Coping Wk(mm) | 0.7 | 0.7 | 1.0 | 0.7 | 1.0 | 0.7 | 1.0 |
| Volume of Shoulder Portion Removed Vd(mm$^3$) | 0 | 0 | 7.0 | 0 | 0 | 0 | 0 |
| Major Radius-Minor Radius Ratio b/a | 1.0 | 1.0 | 0.65 | 1.05 | 1.0 | 0.80 | 0.75 |
| Sm/S | 0.4 | 0.4 | 0.3 | 0.8 | 0.05 | 0.6 | 0.6 |
| H/S | 0.3 | 0.3 | 0.3 | 0.3 | 0.3 | 0.35 | 0.25 |
| Volume of Main Body V(mm$^3$) | 30 | 30 | 23 | 30 | 30 | 35 | 25 |
| Vd/V | 0 | 0 | 0.3 | 0 | 0 | 0 | 0 |
| f(X, Y, Z) | 3.25 | 3.25 | 3.25 | 4.65 | 4.25 | 4.37 | 1.33 |

TABLE 24

| | (Examples) | | | | | | | | |
|---|---|---|---|---|---|---|---|---|---|
| No. | A8 | A9 | A10 | A11 | A12 | A13 | A14 | A15 | A16 |
| Attractive Force F(g) | 670 | 600 | 675 | 533 | 996 | 729 | 540 | 760 | 680 |
| F/V | 33.5 | 30 | 27 | 35.5 | 33.2 | 27 | 25 | 26 | 34 |
| Volume of Main Body V | 20 | 20 | 25 | 15 | 30 | 27 | 21.6 | 30 | 20 |
| Corrosion Resistance | | | | | | | | | |
| Wear Resistance | | | | | | | | | |

TABLE 25

| No. | (Comparative Examples V) | | | | | | |
|---|---|---|---|---|---|---|---|
| | B9 | B10 | B11 | B12 | B13 | B14 | B15 |
| Attractive Force F(g) | 720 | 849 | 345 | 360 | 366 | 459 | 550 |
| F/V | 24 | 28.3 | 15 | 12 | 12.2 | 13.1 | 22.0 |
| Volume of Main Body V | 30 | 30 | 23 | 30 | 30 | 35 | 25 |
| Corrosion Resistance | | X | | | | | |
| Wear Resistance | | X | | | | | |

As seen from Table 23, which shows the results obtained with Comparative Examples V, comparative examples had values of f (X, Y, Z) in the range of 1.33 to 4.65, and the values of the magnetic attractive force per unit volume, F/V, for the comparative examples, except No. B10 with an extremely thin spacer, were in the range of 12 to 24 g/mm$^3$. Besides, a reduction in the volume of the denture attachment was not achieved. As to the corrosion resistance and wear resistance, preferable results were not obtained with the Comparative Example No. B10 having the extremely thin spacer. On the other hand, as seen from Table 22, Examples of the present invention had values of f (X, Y, Z) of not more than 1.0, and values of the magnetic attractive force per unit volume, F/V, in the range of 25 to 35.5 g/mm$^3$, indicating a remarkable improvement in the magnetic attractive force. In addition, the volume of the denture attachment was 15 to 30 mm$^3$, which confirms the achievement of a reduction in the volume of the denture attachment. As to both corrosion resistance and wear resistance, satisfactory results were obtained.

According to the present invention, the dimensional values of the members constituting the denture attachment main body are so set as to satisfy the relationship represented by the specified inequality which ensures a magnetic attractive force of at least 25 g/mm$^3$, whereby it is possible to enhance the magnetic attractive force per unit volume, F/V, from a conventional value of 24 g/mm$^3$ to a value ranging from 25 to 30 g/mm$^3$. It is also possible, by the setting, to reduce the volume of the denture attachment main body from a value of 30 mm$^3$ to a value of 25 mm$^3$ or below. This yields a clinical merit of the denture attachment easily enabling dental treatment for teeth of any size.

What is claimed is:

1. A denture attachment to be embedded in a denture base so as to face a soft magnetic alloy coping embedded in the root of a tooth, the denture attachment comprising:

a spacer formed essentially of a corrosion-resistant non-magnetic alloy, the spacer disposed on the side of the coping;

a pair of end plates formed essentially of a corrosion-resistant soft magnetic alloy, the pair of end plates arranged perpendicularly to the coping with the spacer sandwiched therebetween;

a magnet body disposed on the opposite side of the spacer with respect to the coping, the S and N poles of the magnet body facing the end plates respectively; and a cap covering the magnet body, the pair of end plates and the spacer except on the coping side, the boundary surfaces of the cap and the end plates and the boundary surfaces of the spacer and the end plates being respectively joined together on the side of the coping.

2. The denture attachment as set forth in claim 1, wherein, of each of the pair of end plates, and inner surface opposed to the magnet body is formed as a flat surface, whereas an outer surface covered by the cap is bulged outward in one of a cylindrical shape and prismatic shape; first side surfaces of the spacer and the magnet body opposed to the end plates are each formed as a flat surface to make contact with an inner surface of the end plate, whereas second side surfaces of the spacer and the magnet body are each formed as one of a cylindrical surface and prismatic surface for smooth continuity with an outer surface of the end plate; end faces on one side of the pair of end plates are located flush with an end face of the spacer; and end faces on the other side of the pair of end plates are located flush with an end face of the magnet body.

3. The denture attachment as set forth in claim 2, wherein the boundary surfaces of the cap and the end plates and the boundary surfaces of the end plates and the spacer on the coping side are joined together by one of laser welding and electron beam welding.

4. The denture attachment as set forth in claim 3, wherein the height of the spacer is 0.05 to 1.00 mm, and the depth of weld penetration at the joint portions is at least 0.02 mm and not more than the height of the spacer.

5. The denture attachment as set forth in claim 3, wherein the end plates are formed essentially of a corrosion-resistant soft magnetic alloy containing, by weight, up to 0.03% of C, 11 to 30% of Cr and up to 4% of Mo, and the spacer and the cap are each formed essentially of Ti, a Ti alloy or a non-magnetic stainless steel containing up to 0.03% of C.

6. The denture attachment as set forth in claim 2, wherein that the height of a denture attachment main body comprising the pair of end plates, the spacer and the magnet body joined together is H (mm), the area of a section perpendicular to the height direction of the denture attachment main body is S (mm$^2$), the maximum radius measured from the center of the section is a (mm), the minimum radius measured from the center of the section is b (mm), and the sectional area of the magnet body in the section is Sm (mm$^2$), then the values X, Y and Z defined as $$X=b/a, \ Y=Sm/S, \text{ and } Z=H/S$$

satisfy the following inequality:

$$\frac{(X-0.75)^2}{0.25^2} + \frac{(Y-0.4)^2}{0.35^2} + \frac{(Z-0.15)^2}{0.1^2} \leq 1$$

7. The denture attachment as set forth in claim 6, wherein the thickness of the spacer is 0.05 to 1.0 mm.

8. The denture attachment as set forth in claim 6, wherein a shoulder portion of the end plate is removed in a volume ratio of up to 25% based on the denture attachment main body.

9. The denture attachment as set forth in claim 6, wherein the section perpendicular to the height direction of the denture attachment main body is elliptic in shape.

10. The denture attachment as set forth in claim 1, wherein the magnet body is a rare-earth permanent magnet having a maximum energy product of at least 20 MGOe.

11. The denture attachment as set forth in claim 1, wherein the soft magnetic alloy constituting the end plates has a saturation magnetic flux density of at least 13,000G and a permeability of at least 3,000, whereas the non-magnetic alloys constituting the spacer and the cap have a permeability of not more than 1.2.

12. The denture attachment as set forth in claim 1, wherein the soft magnetic alloy constituting the end plates has a saturation magnetic flux density of at least 20,000G, and the surface thereof for contact with the coping has been subjected to a rustproofing treatment.

* * * * *